US007553668B2

(12) United States Patent
Gonsalves et al.

(10) Patent No.: US 7,553,668 B2

(45) Date of Patent: Jun. 30, 2009

(54) PAPAYA RINGSPOT VIRUS GENES

(75) Inventors: Dennis Gonsalves, Hilo, HI (US); Chu-Hui Chiang, Tainan (TW); Paula F. Tennant, Kingston (JM); Carol V. Gonsalves, Hilo, HI (US); Nonglak Sarindu, Bangkok (TH); Manoel Teixeira Souza, Jr., Nucleo Bandeirante (BR); Osmar Nickel, Goncalves, RS (BR); Gustavo Alberto Fermin-Munoz, Hilo, HI (US); Sanjay Saxena, New Delhi (IN); Wenqi Cai, Beijing (CN)

(73) Assignee: Cornell Research Foundation, Inc., Ithaca, NY (US)

( * ) Notice: Subject to any disclaimer, the term of this patent is extended or adjusted under 35 U.S.C. 154(b) by 196 days.

(21) Appl. No.: 11/456,788

(22) Filed: Jul. 11, 2006

(65) Prior Publication Data

US 2007/0089197 A1 Apr. 19, 2007

Related U.S. Application Data

(62) Division of application No. 10/121,209, filed on Apr. 11, 2002, now Pat. No. 7,078,586.

(60) Provisional application No. 60/283,007, filed on Apr. 11, 2001.

(51) Int. Cl.

*C12N 15/82* (2006.01)
*C12N 5/14* (2006.01)
*C07H 21/04* (2006.01)
*C12N 15/74* (2006.01)

(52) U.S. Cl. ....................... 435/468; 435/419; 435/471; 536/23.72; 800/279

(58) Field of Classification Search ....................... None
See application file for complete search history.

(56) References Cited

U.S. PATENT DOCUMENTS

| | | | |
|---|---|---|---|
| 5,583,021 | A | 12/1996 | Dougherty et al. |
| 5,998,699 | A | 12/1999 | Slightom et al. |
| 6,002,072 | A | 12/1999 | McMaster et al. |
| 6,046,384 | A | 4/2000 | McMaster et al. |
| 6,750,382 | B2 | 6/2004 | Pang et al. |
| 6,903,238 | B2 | 6/2005 | McDevitt et al. |
| 2003/0204869 | A1 | 10/2003 | Gonsalves et al. |

FOREIGN PATENT DOCUMENTS

| | | |
|---|---|---|
| WO | 90/02184 A1 | 3/1990 |
| WO | 96/21019 | 7/1996 |

OTHER PUBLICATIONS

Kertbundit et al., GenBank Accession No. AY0101714, Dec. 20, 2000.*

Purcifull et al., "Papaya Ringspot Virus," *CMI/AAB Descriptions of Plant Viruses*, vol. 292 (No. 84 revised), 8 pp. (1984).

Clark et al., "Characteristics of the Microplate Method of Enzyme-Linked Immunosorbent Assay for the Detection of Plant Viruses," *J. Gen. Virol.* 34:475-483 (1977).

Sanford et al., "The Concept of Parasite-Derived Resistance—Deriving Resistance Genes from the Parasite's Own Genome," *J. Theor. Biol.* 113:395-405 (1985).

Powell Abel et al., "Delay of Disease Development in Transgenic Plants That Express the Tobacco Mosaic Virus Coat Protein Gene," *Science* 232:738-743 (1986).

Golemboski et al., "Plants Transformed With a Tobacco Mosaic Virus Nonstructural Gene Sequence are Resistant to the Virus," *Proc. Natl. Acad. Sci.* 87:6311-6315 (1990).

Beck et al., "Disruption of Virus Movement Confers Board-Spectrum Resistance Against Systemic Infection by Plant Viruses with a Triple Gene Block," *Proc. Natl. Acad. Sci.* 91:10310-10314 (1994).

Nelson et al., "Virus Tolerance, Plant Growth, and Field Performance of Transgenic Tomato Plants Expressing Coat Protein from Tobacco Mosaic Virus," *Biotechnology* 6:403-409 (1988).

Stark et al., "Protection Against Potyvirus Infection in Transgenic Plants: Evidence for Broad Spectrum Resistance," *Biotechnology* 7:1257-1262 (1989).

Manshardt, "Papaya," in *Papaya in Biotechnology of Perennial Fruit Crops*, Hammerschlag, ed., Wallingford, UK: CAB Int., Chapter 21:489-511 (1992).

Fitch et al., "Virus Resistant Papaya Plants Derived from Tissues Bombarded with the Coat Protein Gene of Papaya Ringspot Virus," *Biotechnology* 10:1466-1472 (1992).

Maiti et al., "Plants that Express a Potyvirus Proteinase Gene are Resistant to Virus Infection," *Proc. Natl. Acad. Sci.* 90:6110-6114 (1993).

Grumet, "Development of Virus Resistant Plants via Genetic Engineering," *Plant Breeding Reviews* 12:47-79 (1994).

Tennant et al., "Differential Protection Against Papaya Ringspot Virus Isolates in Coat Protein Gene Transgenic Papaya and Classically Cross-Protected Papaya," *Phytopathology* 84:1359-1366 (1994).

Dougherty et al., "Transgenes and Gene Suppression: Telling Us Something New?" *Current Opinion in Cell Biology* 7:399-405 (1995).

Lomonossoff, "Pathogen-Derived Resistance to Plant Viruses," *Annu. Rev. Phytopathol.* 33:323-343 (1995).

Baulcombe, "Mechanisms of Pathogen-Derived Resistance to Viruses in Transgenic Plants," *The Plant Cell* 8:1833-1844 (1996).

(Continued)

*Primary Examiner*—Ashwin Mehta
(74) *Attorney, Agent, or Firm*—Nixon Peabody LLP

(57) ABSTRACT

The present invention relates to the isolation and identification of nucleic acid sequences encoding the coat protein of papaya ringspot virus in the Kapoho (KA), Keaau (KE), Thailand (TH), Brazil (BR), Jamaica (JA), Mexico (ME), Venezuela (VE), and Oahu (OA) strains, and the uses thereof to impart viral resistance to papaya plants. The present invention also relates to nucleic acid constructs containing individual or multiple papaya ringspot virus coat protein-encoding nucleic acid sequences, and host cells and transgenic plants and seeds containing such constructs. The present invention is also directed to a method of using such constructs to impart to plants resistance to papaya ringspot virus.

12 Claims, 5 Drawing Sheets

OTHER PUBLICATIONS

Lius et al., "Pathogen-Derived Resistance Provides Papaya with Effective Protection Against Papaya Ringspot Virus," *Molecular Breeding* 3:161-168 (1997).
Gonsalves, "Control of Papaya Ringspot Virus in Papaya: A Case Study," *Annu. Rev. Phytopathol.* 36:415-37 (1998).
Fuchs et al., "Resistance of Transgenic Hybrid Squash ZW-20 Expressing the Coat Protein Gene of Zucchini Yellow Mosaic Virus and Watermelon Mosaic Virus 2 to Mixed Infections by Both Potyviruses," *Bio/Technology* 13:1466-1473 (1995).
Tricoli et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus," *Bio/Technology* 13:1458-1465 (1995).
Wang et al., "Comparison of the Nuclear Inclusion b Protein and Coat Protein Genes of Five Papaya Ringspot Virus Strains Distinct in Geographic Origin and Pathogenicity," *The American Phytopathological Society* 84(10):1205-1210 (1994).
Bateson et al., "The Nucleotide Sequence of the Coat Protein Gene and 3' Untranslated Region of Papaya Ringspot Virus Type W (Aust)," *Arch. Virol.* 123:101-109 (1992).
Jan et al., "A Minimum Length of N Gene Sequence in Transgenic Plants Is Required for RNA-Mediated Tospovirus Resistance," *Journal of General Virology* 81: 235-242 (2000).
Bateson et al., "Papaya Ringspot Potyvirus: Isolate Variability and the Origin of PRSV Type P (Australia)," *Journal of General Virology* 75:3547-3553 (1994).
Ling et al., "Protection Against Detrimental Effects of Potyvirus Infection in Transgenic Tobacco Plants Expressing the Papaya Ringspot Virus Coat Protein Gene," *Bio/Technology* 9:752-758 (1991).
Quemada et al., "The Nucleotide Sequences of the 3'-Terminal Regions of Papaya Ringspot Virus Strains W and P," *Journal of General Virology* 71:203-210 (1990).
Junjun et al., "Study of Replicase (Subunit) Gene of Papaya Ringspot Virus Cloning, Sequencing and Construction of Higher Plant Expression Vector," *Chinese Journal of Biotechnology* 10(3): 219-224 (1994).
Yeh et al., "Complete Nucleotide Sequence and Genetic Organization of Papaya Ringspot Virus RNA," *Journal of General Virology* 73:2531-2541 (1992).
Nagel et al., "Complementary DNA Cloning and Expression of the Papaya Ringspot Potyvirus Sequences Encoding Capsid Protein and a Nuclear Inclusion-Like Protein in *Escherichia coli*, "*Virology* 143: 435-441 (1985).
Waterhouse et al., "Virus Resistance and Gene Silencing in Plants Can Be Induced by Simultaneous Expression of Sense and Antisense RNA," *Proc. Natl. Acad. Sci. USA* 95:13959-13964 (1998).
Martin, D., "Papaya Production Statistics," *Proc. Annu. Hawaii Papaya Ind. Assoc. Conf., 39th, Kihei*, pp. 31-36, Sep. 23-24, 1994.
Galinsky, "World Market for Papaya," *Reg. Agribus. Proj. Mark. Inf. Bull.*, Feb. No. 12, 5 pp. (1996).
Voinnet, O., "RNA Silencing as a Plant Immune System Against Viruses," *Trends in Genetics* 17:449-459 (2001).
Voinnet & Baulcombe, "Systemic Signalling in Gene Silencing," *Nature* 389:553 (1997).
GenBank Accession No. X67672 S49774, Yeh et al.
GenBank Accession No. X67673, Wang et al.
Cheng et al., "Efficient Transformation of Papaya by Coat Protein Gene of Papaya Ringspot Virus Mediated by *Agrobacterium* Following Liquid-Phase Wounding of Embryogenic Tissues with Carborundum," *Plant Cell Reports* 16:127-132 (1996).
Silva-Rosales et al., *Arch. Virol.* 145:835-843 (2000).
Pang et al., *PNAS* 94:861-8266 (1997).
Voinnet et al., *PNAS* 96:14171-14152 (1999).
Tenant et al., *Eur. J. Plant Pathol.* 107:645-653 (2001).
Maoka et al., *Arch. Virol.* 141:197-204 (1996).
Cai et al., *In Vitro Cell Dev. Biol. Plant* 35:61-69 (1999).
Anandalaksmi et al., *Proc. Natl. Acad. USA* 95:13079 (1998) (abstract only).
Kasschau et al., *Cell* 95:461 (1998) (abstract only).
Llave et al., *Proc. Natl. Acad. Sci. USA* 97:13401 (2000) (abstract only).

* cited by examiner

A

B

SEQUENCE LISTING

```
<160> NUMBER OF SEQ ID NOS: 36

<210> SEQ ID NO 1
<211> LENGTH: 864
<212> TYPE: DNA
<213> ORGANISM: PRSV-KA-CP

<400> SEQUENCE: 1

tccaagaatg aagctgtgga tgctggtttg aatgaaaaac tcaaagagaa agaaagacag      60

aaagaaaaag aaaaagaaaa acaaaaagaa aaaggaaaag acgatgctag tgacgaaaat     120

gatgtgtcaa ctagcacaaa aactggagag agagatagag atgtcaatgt tgggaccagt     180

ggaactttcg ctgttccgag aattaaatca tttactgata agttgattct accaagaatt     240

aagggaaaga ctgtccttaa tttaagtcat cttcttcagt ataatccgca acaaattgac     300

atttctaaca ctcgtgccac tcagtcacaa tttgagaagt ggtatgaggg agtgagggat     360

gattatggcc ttaatgataa tgaaatgcaa gttatgctaa atggtttgat ggtttggtgt     420

atcgagaatg gtacatctcc agacatatct ggtgtatggg ttatgatgga tggggaaacc     480

caagttgatt atccaaccaa gcctttaatt gagcatgata ctccgtcatt taggcaaatt     540

atggctcact ttagtaacgc ggcagaagca tacattgcga agagaaatgc tactgagagg     600

tacatgccgc ggtacggaat caagagaaat ttgactgaca ttagcctcgc tagatatgct     660

ttcgacttct atgaggtgaa ttcgaaaaca cctgataggg ctcgcgaagc ccacatgcag     720

atgaaggctg cagcgctgcg aaacactagt cgcagaatgt ttggtatgga cggcagtgtt     780

agtaacaagg aagaaaacac ggagagacac acagtggaag atgtcgatag agacatgcac     840

tctctcctgg gtatgcgcaa ctaa                                            864


<210> SEQ ID NO 2
<211> LENGTH: 287
<212> TYPE: PRT
<213> ORGANISM: PRSV-KA-CP

<400> SEQUENCE: 2

Ser Lys Asn Glu Ala Val Asp Ala Gly Leu Asn Glu Lys Leu Lys Glu
  1               5                  10                  15

Lys Glu Arg Gln Lys Glu Lys Glu Lys Glu Lys Gln Lys Glu Lys Gly
             20                  25                  30

Lys Asp Asp Ala Ser Asp Glu Asn Asp Val Ser Thr Ser Thr Lys Thr
         35                  40                  45

Gly Glu Arg Asp Arg Asp Val Asn Val Gly Thr Ser Gly Thr Phe Ala
     50                  55                  60

Val Pro Arg Ile Lys Ser Phe Thr Asp Lys Leu Ile Leu Pro Arg Ile
```

-continued

```
 65                  70                  75                  80

Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Asp Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asp Arg Asp Met His Ser Leu Leu Gly Met Arg Asn
        275                 280                 285


<210> SEQ ID NO 3
<211> LENGTH: 861
<212> TYPE: DNA
<213> ORGANISM: PRSV-TH-CP

<400> SEQUENCE: 3

tccaagaatg aagctgtgga tgctggtctt aatgagaagt tcaaagataa agaaaaacag      60

aaagaagaaa aagataaaca aaaaggtaaa gaaaataatg aagctagtga cggaaatgat     120

gtgtcaacta gcacaaaaac tggagagaga gatagagatg tcaatgccgg aactagtggt     180

actttcactg ttccgagaat aaaattattt accgacaaga tgattttacc aagaattaag     240

ggaaaaactg tccttagttt aaatcatctt cttcagtata atccgcaaca aatagacatc     300

tcaaacactc gtgccactca atctcaattc gaaaagtggt atgagggagt gaggaatgat     360

tacggtctta atgataacga aatgcaagtg atgttaaatg gtttgatggt ttggtgcatc     420

gaaaatggaa catccccaga catatctggt gtctgggtga tgatggatgg ggaaacccaa     480

gtcgattatc ccatcaagcc tttgatcgaa catgcaactc cttcgttcag gcaaatcatg     540

gctcacttca gtaacgcggc agaggcatac atcgcaaaga ggaatgctac tgagaggtac     600

atgccgcggt atggaatcaa gaggaatctg actgacatta gtctcgctag atatgctttc     660

gacttctatg aggtgaactc aaaaacacct gatagggctc gtgaagctca tatgcagatg     720

aaggctgcag cgctgcgcaa cactgatcgc agaatgtttg gaatggacgg cagtgtcagt     780

aacaaggaag aaaacacgga gagacacaca gtggaagatg tcaacagaga catgcactct     840

ctcctaggta tgcgcaattg a                                               861
```

-continued

<210> SEQ ID NO 4
<211> LENGTH: 286
<212> TYPE: PRT
<213> ORGANISM: PRSV-TH-CP

<400> SEQUENCE: 4

```
Ser Lys Asn Glu Ala Val Asp Ala Gly Leu Asn Glu Lys Phe Lys Asp
  1               5                  10                  15
Lys Glu Lys Gln Lys Glu Glu Lys Asp Lys Gln Lys Gly Lys Glu Asn
             20                  25                  30
Asn Glu Ala Ser Asp Gly Asn Asp Val Ser Thr Ser Thr Lys Thr Gly
         35                  40                  45
Glu Arg Asp Arg Asp Val Asn Ala Gly Thr Ser Gly Thr Phe Thr Val
     50                  55                  60
Pro Arg Ile Lys Leu Phe Thr Asp Lys Met Ile Leu Pro Arg Ile Lys
 65                  70                  75                  80
Gly Lys Thr Val Leu Ser Leu Asn His Leu Leu Gln Tyr Asn Pro Gln
                 85                  90                  95
Gln Ile Asp Ile Ser Asn Thr Arg Ala Thr Gln Ser Gln Phe Glu Lys
            100                 105                 110
Trp Tyr Glu Gly Val Arg Asn Asp Tyr Gly Leu Asn Asp Asn Glu Met
        115                 120                 125
Gln Val Met Leu Asn Gly Leu Met Val Trp Cys Ile Glu Asn Gly Thr
    130                 135                 140
Ser Pro Asp Ile Ser Gly Val Trp Val Met Met Asp Gly Glu Thr Gln
145                 150                 155                 160
Val Asp Tyr Pro Ile Lys Pro Leu Ile Glu His Ala Thr Pro Ser Phe
                165                 170                 175
Arg Gln Ile Met Ala His Phe Ser Asn Ala Ala Glu Ala Tyr Ile Ala

            180                 185                 190
Lys Arg Asn Ala Thr Glu Arg Tyr Met Pro Arg Tyr Gly Ile Lys Arg

        195                 200                 205
Asn Leu Thr Asp Ile Ser Leu Ala Arg Tyr Ala Phe Asp Phe Tyr Glu

    210                 215                 220
Val Asn Ser Lys Thr Pro Asp Arg Ala Arg Glu Ala His Met Gln Met

225                 230                 235                 240
Lys Ala Ala Ala Leu Arg Asn Thr Asp Arg Arg Met Phe Gly Met Asp

                245                 250                 255
Gly Ser Val Ser Asn Lys Glu Glu Asn Thr Glu Arg His Thr Val Glu

            260                 265                 270
Asp Val Asn Arg Asp Met His Ser Leu Leu Gly Met Arg Asn
        275                 280                 285
```

<210> SEQ ID NO 5
<211> LENGTH: 921
<212> TYPE: DNA
<213> ORGANISM: PRSV-KE-CP1

<400> SEQUENCE: 5

```
tcaaggagca ctgatgatta tcaacttgtt tggagtgaca atacacatgt gtttcatcag     60

tccaagaatg aagctgtgga tgctggtttg aatgaaaaac tcaaagagaa agaaaaacag    120

aaagaaaaag aaaaagaaaa acaaaaagaa aaaggaagag acgatgctag tgacgaaaat    180

gatgtgtcaa ctagcacaaa aactggagag agagatagag atgtcaatgt tgggaccagt    240

ggaactttcg ctgttccgag aattaaatca tttactgata agttgattct accaagaatt    300

aagggaaaga ctgtccttaa tttaagtcat cttcttcagt ataatccgca acaaattgac    360

atttctaaca ctcgtgccac tcagtcacaa tttgagaagt ggtatgaggg agtgagggat    420

gattatggcc ttaatgataa tgaaatgcaa gttatgctaa atggtttgat ggtttggtgt    480

atcgagaatg gtacatctcc agacatatct ggtgtatggg ttatgatgga tggggaaacc    540

caagttgatt atccaaccaa gcctttaatt gagcatgcta ctccgtcatt taggcaaatt    600
```

-continued

```
atggctcact ttagtaacgc ggcagaagca tacattgcga agagaaatgc tactgagagg    660

tacatgccgc ggtacggaat caagagaaat ttgactgacg ttagcctcgc tagatatgct    720

ttcgacttct atgaggtgaa ttcgaaaaca cctgataggg ctcgcgaagc ccacatgcag    780

atgaaggctg cagcgctgcg aaacactagt cgcagaatgt ttggtatgga cggcagtgtt    840

agtaacaagg aagaaaacac ggagagacac acagtggaag atgtcaatag agacatgcac    900

tctctcctgg gcatgcgcaa c                                              921


<210> SEQ ID NO 6
<211> LENGTH: 864
<212> TYPE: DNA
<213> ORGANISM: PRSV-KE-CP2

<400> SEQUENCE: 6

tccaagaatg aagctgtgga tgctggtttg aatgaaaaac tcaaagagaa agaaaaacag     60

aaagaaaaag aaaaagaaaa acaaaaagaa aaaggaaaag acgatgctag tgacgaaaat    120

gatgtgtcaa ctagcacaaa aactggagag agagatagag atgtcaatgt tgggaccagt    180

ggaactttcg ctgttccgag aattaaatca tttactgata agttgattct accaagaatt    240

aagggaaaga ctgtccttaa tttaagtcat cttcttcagt ataatccgca acaaattgac    300

atttctaaca ctcgtgccac tcagtcacaa tttgagaagt ggtatgaggg agtgagggat    360

gattatggcc ttaatgataa tgaaatgcaa gttatgctaa atggtttgat ggtttggtgt    420

atcgagaatg gtacatctcc agacatatct ggtgtatggg ttatgatgga tggggaaacc    480

caagttgatt atccaaccaa gcctttaatt gagcatgcta ctccgtcatt taggcaaatt    540

atggctcact ttagtaacgc ggcagaagca tacattgcga agagaaatgc tactgagagg    600

tacatgccgc ggtacggaat caagagaaat ttgactgacg ttagcctcgc tagatatgct    660

ttcgacttct atgaggtgaa ttcgaaaaca cctgataggg ctcgcgaagc ccacatgcag    720

atgaaggctg cagcgctgcg aaacactagt cgcagaatgt ttggtatgga cggcagtgtt    780

agtaacaagg aagaaaacac ggagagacac acagtggaag atgtcaatag agacatgcac    840

tctctcctgg gcatgcgcaa ctaa                                           864


<210> SEQ ID NO 7
<211> LENGTH: 307
<212> TYPE: PRT
<213> ORGANISM: PRSV-KE-CP1

<400> SEQUENCE: 7

Ser Arg Ser Thr Asp Asp Tyr Gln Leu Val Trp Ser Asp Asn Thr His
  1               5                  10                  15

Val Phe His Gln Ser Lys Asn Glu Ala Val Asp Ala Gly Leu Asn Glu
             20                  25                  30

Lys Leu Lys Glu Lys Glu Lys Gln Lys Glu Lys Glu Lys Glu Lys Gln
         35                  40                  45

Lys Glu Lys Gly Arg Asp Asp Ala Ser Asp Glu Asn Asp Val Ser Thr
     50                  55                  60

Ser Thr Lys Thr Gly Glu Arg Asp Arg Asp Val Asn Val Gly Thr Ser
 65                  70                  75                  80

Gly Thr Phe Ala Val Pro Arg Ile Lys Ser Phe Thr Asp Lys Leu Ile
                 85                  90                  95

Leu Pro Arg Ile Lys Gly Lys Thr Val Leu Asn Leu Ser His Leu Leu
            100                 105                 110
```

-continued

```
Gln Tyr Asn Pro Gln Gln Ile Asp Ile Ser Asn Thr Arg Ala Thr Gln
        115                 120                 125

Ser Gln Phe Glu Lys Trp Tyr Glu Gly Val Arg Asp Asp Tyr Gly Leu
    130                 135                 140

Asn Asp Asn Glu Met Gln Val Met Leu Asn Gly Leu Met Val Trp Cys
145                 150                 155                 160

Ile Glu Asn Gly Thr Ser Pro Asp Ile Ser Gly Val Trp Val Met Met
                165                 170                 175

Asp Gly Glu Thr Gln Val Asp Tyr Pro Thr Lys Pro Leu Ile Glu His
            180                 185                 190

Ala Thr Pro Ser Phe Arg Gln Ile Met Ala His Phe Ser Asn Ala Ala
        195                 200                 205

Glu Ala Tyr Ile Ala Lys Arg Asn Ala Thr Glu Arg Tyr Met Pro Arg
    210                 215                 220

Tyr Gly Ile Lys Arg Asn Leu Thr Asp Val Ser Leu Ala Arg Tyr Ala
225                 230                 235                 240

Phe Asp Phe Tyr Glu Val Asn Ser Lys Thr Pro Asp Arg Ala Arg Glu
                245                 250                 255

Ala His Met Gln Met Lys Ala Ala Ala Leu Arg Asn Thr Ser Arg Arg
            260                 265                 270

Met Phe Gly Met Asp Gly Ser Val Ser Asn Lys Glu Glu Asn Thr Glu
        275                 280                 285

Arg His Thr Val Glu Asp Val Asn Arg Asp Met His Ser Leu Leu Gly
    290                 295                 300

Met Arg Asn
305


<210> SEQ ID NO 8
<211> LENGTH: 287
<212> TYPE: PRT
<213> ORGANISM: PRSV-KE-CP2

<400> SEQUENCE: 8

Ser Lys Asn Glu Ala Val Asp Ala Gly Leu Asn Glu Lys Leu Lys Glu
  1               5                  10                  15

Lys Glu Lys Gln Lys Glu Lys Glu Lys Glu Lys Gln Lys Glu Lys Gly
            20                  25                  30

Lys Asp Asp Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Ala
     50                  55                  60

Val Pro Arg Ile Lys Ser Phe Thr Asp Lys Leu Ile Leu Pro Arg Ile
 65                  70                  75                  80

Lys Gly Lys Thr Val Leu Asn Leu Ser His Leu Leu Gln Tyr Asn Pro
                 85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Ala Thr Pro Ser
                165                 170                 175
```

-continued

```
Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Val Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

<210> SEQ ID NO 9
<211> LENGTH: 864
<212> TYPE: DNA
<213> ORGANISM: PRSV-YK-CP

<400> SEQUENCE: 9

```
tctaaaaatg aagctgtgga taccggtctg aatgagaagc tcaaagaaaa agaaaagcag      60

aaagaaaaag aaaaagataa acaacaagat aaagacaatg atggagctag tgacggaaac     120

gatgtgtcaa ctagcacaaa aactggagag agagataggg atgtcaatgc cggaactagt     180

ggaaccttca ctgttccgag gataaagtca tttactgata agatgatctt accaagaatt     240

aagggaaaaa ctgtccttaa tttaaatcat cttcttcagt ataatccgaa acaagttgac     300

atctcaaaca ctcgcgccac tcaatctcaa tttgagaagt ggtatgaggg agtgagaaat     360

gattatggcc ttaatgataa cgaaatgcaa gtaatgttaa atggtttgat ggtttggtgt     420

atcgaaaatg gtacatctcc agatatatct ggtgtctggg ttatgatgga tggggaaacc     480

caagtcgatt atcccattaa acctttgatt gaacacgcaa ctccttcatt taggcaaatc     540

atggctcact tcagtaacgc ggcagaggca tacatcgcga agaggaatgc aactgagaag     600

tacatgccgc ggtatggaat caagagaaat ttgactgaca ttagtctcgc tagatatgct     660

ttcgatttct atgaggtgaa ttcgaaaaca cctgataggg ctcgtgaagc tcatatgcag     720

atgaaggctg cagcgctacg caatactaat cgcaaaatgt ttggaatgga cggcagtgtc     780

agtaacaagg aagaaaacac ggagagacac acagtggaag atgtcaacag agacatgcac     840

tctctcctgg gtatgcgcaa ttga                                            864
```

<210> SEQ ID NO 10
<211> LENGTH: 287
<212> TYPE: PRT
<213> ORGANISM: PRSV-YK-CP

<400> SEQUENCE: 10

```
Ser Lys Asn Glu Ala Val Asp Thr Gly Leu Asn Glu Lys Leu Lys Glu
  1               5                  10                  15

Lys Glu Lys Gln Lys Glu Lys Glu Lys Asp Lys Gln Gln Asp Lys Asp
             20                  25                  30

Asn Asp Gly Ala Ser Asp Gly Asn Asp Val Ser Thr Ser Thr Lys Thr
         35                  40                  45

Gly Glu Arg Asp Arg Asp Val Asn Ala Gly Thr Ser Gly Thr Phe Thr
     50                  55                  60
```

-continued

```
Val Pro Arg Ile Lys Ser Phe Thr Asp Lys Met Ile Leu Pro Arg Ile
 65                  70                  75                  80

Lys Gly Lys Thr Val Leu Asn Leu Asn His Leu Leu Gln Tyr Asn Pro
                 85                  90                  95

Lys Gln Val Asp Ile Ser Asn Thr Arg Ala Thr Gln Ser Gln Phe Glu
            100                 105                 110

Lys Trp Tyr Glu Gly Val Arg Asn Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Lys Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Lys Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

<210> SEQ ID NO 11
<211> LENGTH: 855
<212> TYPE: DNA
<213> ORGANISM: PRSV-ME-CP

<400> SEQUENCE: 11

```
tccaagaatg aagctgtgga tgctggtttg aatgaaaaac tcaaagaaaa agaaaaacag     60

aaagaaaaag aaaaacaaaa agaaaaagaa aaagacaatg ctagtgacgg aaatgatgtg    120

tcgactagca caaaaactgg agagaaagat agagatgtca atgtcggaac tagtggaact    180

ttcactgttc cgagaattaa atcatttact gataagatga ttctaccgag aattaaggga    240

aagactgtcc ttaatttaaa tcatcttctt cagtataatc cgcaacaaat tgatatttct    300

aacactcgtg ccactcagtc acaatttgag aaatggtatg agggagtgag gaatgattat    360

ggtctgaatg ataatgaaat gcaagtgatg ctgaatggct tgatggtttg gtgtatcgag    420

aatggtacat ctccagacat atctggtgtt tgggttatga tggatgggga aattcaagtt    480

gactatccaa tcaagcctct aattgagcat gctaccccgt catttaggca gattatggct    540

cactttagta acgcggcaga agcatatatt gcaaagagaa atgccactga gaggtacatg    600

ccgcggtatg gaatcaagag aaatttgact gacattagcc tcgctaggta cgctttcgat    660

ttctatgagg ttaattcgaa aacacctgat agggctcgcg aagctcacat gcagatgaaa    720

gctgcagcgc tgcgaaacac tagtcgcaga atgtttggta tgggcggcag tgttagtaac    780

aaggaagaaa acacggaaag acacacagtg gaagatgtca atagagacat gcactctctc    840
```

-continued

```
ctgggtatgc gcaac                                                     855


<210> SEQ ID NO 12
<211> LENGTH: 285
<212> TYPE: PRT
<213> ORGANISM: PRSV-ME-CP

<400> SEQUENCE: 12

Ser Lys Asn Glu Ala Val Asp Ala Gly Leu Asn Glu Lys Leu Lys Glu
  1               5                  10                  15

Lys Glu Lys Gln Lys Glu Lys Glu Lys Gln Lys Glu Lys Glu Lys Asp
             20                  25                  30

Asn Ala Ser Asp Gly Asn Asp Val Ser Thr Ser Thr Lys Thr Gly Glu
         35                  40                  45

Lys Asp Arg Asp Val Asn Val Gly Thr Ser Gly Thr Phe Thr Val Pro
     50                  55                  60

Arg Ile Lys Ser Phe Thr Asp Lys Met Ile Leu Pro Arg Ile Lys Gly
 65                  70                  75                  80

Lys Thr Val Leu Asn Leu Asn His Leu Leu Gln Tyr Asn Pro Gln Gln
                 85                  90                  95

Ile Asp Ile Ser Asn Thr Arg Ala Thr Gln Ser Gln Phe Glu Lys Trp
            100                 105                 110

Tyr Glu Gly Val Arg Asn Asp Tyr Gly Leu Asn Asp Asn Glu Met Gln
        115                 120                 125

Val Met Leu Asn Gly Leu Met Val Trp Cys Ile Glu Asn Gly Thr Ser
    130                 135                 140

Pro Asp Ile Ser Gly Val Trp Val Met Met Asp Gly Glu Ile Gln Val
145                 150                 155                 160

Asp Tyr Pro Ile Lys Pro Leu Ile Glu His Ala Thr Pro Ser Phe Arg
                165                 170                 175

Gln Ile Met Ala His Phe Ser Asn Ala Ala Glu Ala Tyr Ile Ala Lys
            180                 185                 190

Arg Asn Ala Thr Glu Arg Tyr Met Pro Arg Tyr Gly Ile Lys Arg Asn
        195                 200                 205

Leu Thr Asp Ile Ser Leu Ala Arg Tyr Ala Phe Asp Phe Tyr Glu Val
    210                 215                 220

Asn Ser Lys Thr Pro Asp Arg Ala Arg Glu Ala His Met Gln Met Lys
225                 230                 235                 240

Ala Ala Ala Leu Arg Asn Thr Ser Arg Arg Met Phe Gly Met Gly Gly
                245                 250                 255

Ser Val Ser Asn Lys Glu Glu Asn Thr Glu Arg His Thr Val Glu Asp
            260                 265                 270

Val Asn Arg Asp Met His Ser Leu Leu Gly Met Arg Asn
        275                 280                 285


<210> SEQ ID NO 13
<211> LENGTH: 861
<212> TYPE: DNA
<213> ORGANISM: PRSV-BR-CP

<400> SEQUENCE: 13

tccaaaaatg aagctgtgga tgctggtttg aatgaaaagc gtaaagaaca agagaaacaa      60

gaagaaaaag aagaaaaaca aaaaaagaaa gaaaaagacg atgctagtta cggaaacgat     120

gtgtcaacta gcacaagaac tggagagaga gacagagatg tcaatgttgg gaccagtgga     180

actttcactg ttccgagaac aaaatcattt actgataaga tgattttacc tagaattaag     240
```

-continued

```
ggaaaaactg tccttaattt aaatcatctg attcagtata atccgcaaca aattgacatt    300

tctaacactc gtgctactca atcacaattt gagaagtggt acgagggagt gaggaatgat    360

tatggcctta atgataatga gatgcaaata gtgctaaatg gtttgatggt ttggtgtatc    420

gaaaacggta catctccaga catatctggt gtctgggtta tgatggatgg ggaaacccag    480

gttgactatc caatcaagcc tttaattgag catgctactc cgtcgtttag gcaaattatg    540

gctcatttca gtaacgcggc agaagcatac attacaaaga gaaatgctac tgagaggtac    600

atgccgcggt atgggatcaa gagaaatttg actgacatta gtcttgctag atatgctttc    660

gatttctatg aggtgaattc gaaaacacct gatagggctc gcgaagctca catgcagatg    720

aaagctgcag cgctgcgaaa cactaatcgc agaatgtttg gtatggacgg cagtgttagt    780

aacaaggaag aaaacacgga gagacacaca gtggaagatg tcaatagaga catgcactct    840

ctcctgggta tgcgcaactg a                                              861
```

```
<210> SEQ ID NO 14
<211> LENGTH: 286
<212> TYPE: PRT
<213> ORGANISM: PRSV-BR-CP

<400> SEQUENCE: 14

Ser Lys Asn Glu Ala Val Asp Ala Gly Leu Asn Glu Lys Arg Lys Glu
  1               5                  10                  15

Gln Glu Lys Gln Glu Glu Lys Glu Glu Lys Gln Lys Lys Lys Glu Lys
             20                  25                  30

Asp Asp Ala Ser Tyr Gly Asn Asp Val Ser Thr Ser Thr Arg Thr Gly
         35                  40                  45

Glu Arg Asp Arg Asp Val Asn Val Gly Thr Ser Gly Thr Phe Thr Val
     50                  55                  60

Pro Arg Thr Lys Ser Phe Thr Asp Lys Met Ile Leu Pro Arg Ile Lys
 65                  70                  75                  80

Gly Lys Thr Val Leu Asn Leu Asn His Leu Ile Gln Tyr Asn Pro Gln
                 85                  90                  95

Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Ile Val Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Thr
            180                 185                 190

Lys Arg Asn Ala Thr Glu Arg Tyr Met Pro Arg Tyr Gly Ile Lys Arg
        195                 200                 205

Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asn Arg Arg Met Phe Gly Met Asp
                245                 250                 255
```

-continued

```
Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285
```

<210> SEQ ID NO 15
<211> LENGTH: 864
<212> TYPE: DNA
<213> ORGANISM: PRSV-JA-CP

<400> SEQUENCE: 15

```
tctaaaaatg aagctgtgga tgctggttta aatgaaaagc tcaaagaaaa agaaaaacag      60

aaagataaag aaaaagaaaa acaaaaagat aaagaaaaag gagatgctag tgacggaaat     120

gatggttcga ctagcacaaa aactggagag agagatagag atgtcaatgt tgggaccagt     180

ggaacttcca ctgttccgag aattaaatca ttcactgata agatggttct accaagaatt     240

aagggaaaaa ctgtccttaa tttaaatcat cttcttcagt ataatccaca acaaattgac     300

atttctaaca ctcgtgccac tcagtcacaa tttgagaagt ggtacgaagg agtgaggagt     360

gattatggcc taaatgatag tgaaatgcaa gtgacgctaa atggcttgat ggtttggtgt     420

atcgagaatg gtacatctcc agacatatct ggtgtctggg ttatgatgga tggggaaacc     480

caagttgatt atccaatcaa gcctttaatt gagcacgcta ccccatcatt taggcagatt     540

atggctcact tcagtaacgc ggcagaagca tacactgcaa agagaaatgc tactgagagg     600

tacatgccgc ggtatggaat caagagaaat ttgactgaca ttagtctcgc tagatacgct     660

ttcgatttct atgaggtgaa ttcgaagaca cctgataggg ctcgtgaagc tcacatgcag     720

atgaaagctg cagcgctgcg aaacactaat cgcagaatgt ttggtatgga cggcagtgtt     780

agtaacaatg aagaaaacac ggagagacac acagtggaag atgtctatat agacatgcac     840

tctctcctgc gtttgcgcaa ctga                                            864
```

<210> SEQ ID NO 16
<211> LENGTH: 287
<212> TYPE: PRT
<213> ORGANISM: PRSV-JA-CP

<400> SEQUENCE: 16

```
Ser Lys Asn Glu Ala Val Asp Ala Gly Leu Asn Glu Lys Leu Lys Glu
  1               5                  10                  15

Lys Glu Lys Gln Lys Asp Lys Glu Lys Glu Lys Gln Lys Asp Lys Glu
             20                  25                  30

Lys Gly Asp Ala Ser Asp Gly Asn Asp Gly Ser Thr Ser Thr Lys Thr
         35                  40                  45

Gly Glu Arg Asp Arg Asp Val Asn Val Gly Thr Ser Gly Thr Ser Thr
     50                  55                  60

Val Pro Arg Ile Lys Ser Phe Thr Asp Lys Met Val Leu Pro Arg Ile
 65                  70                  75                  80

Lys Gly Lys Thr Val Leu Asn Leu Asn His Leu Leu Gln Tyr Asn Pro
                 85                  90                  95

Gln Gln Ile Asp Ile Ser Asn Thr Arg Ala Thr Gln Ser Gln Phe Glu
            100                 105                 110

Lys Trp Tyr Glu Gly Val Arg Ser Asp Tyr Gly Leu Asn Asp Ser Glu
        115                 120                 125

Met Gln Val Thr Leu Asn Gly Leu Met Val Trp Cys Ile Glu Asn Gly
    130                 135                 140
```

-continued

```
Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Thr
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Arg Met Phe Gly Met
                245                 250                 255

Asp Gly Ser Val Ser Asn Asn Glu Glu Asn Thr Glu Arg His Thr Val
            260                 265                 270

Glu Asp Val Tyr Ile Asp Met His Ser Leu Leu Arg Leu Arg Asn
        275                 280                 285


<210> SEQ ID NO 17
<211> LENGTH: 864
<212> TYPE: DNA
<213> ORGANISM: PRSV-OA-CP

<400> SEQUENCE: 17

tccaagaatg aagctgtgga tgctggtttg aatgaaaaat tcaaagagaa ggaaaaacag      60

aaagaaaaag aaaaagaaaa acaaaaagag aaagaaaaag atggtgctag tgacgaaaat     120

gatgtgtcaa ctagcacaaa aactggagag agagatagag atgtcaatgt cgggaccagt     180

ggaactttca cagttccgag aattaaatca tttactgata agatgattct accgagaatt     240

aaggggaagg ctgtccttaa tttaaatcat cttcttcagt acaatccgca acaaatcgac     300

atttctaaca ctcgtgccgc tcattcacaa tttgaaaagt ggtatgaggg agtgaggaat     360

gattatgccc ttaatgataa tgaaatgcaa gtgatgctaa atggtttgat ggtttggtgt     420

atcgagaatg gtacatctcc agacatatct ggtgtctggg taatgatgga tggggaaacc     480

caagtcgatt atccaatcaa gcctttgatt gagcatgcta ctccgtcatt taggcaaatt     540

atggctcact ttagtaacgc ggcagaagca tacattgcga agagaaatgc tactgagagg     600

tacatgccgc ggtatggaat caagagaaat ttgactgaca ttagcctcgc tagatacgct     660

ttcgactttt atgaggtgaa ttcgaaaaca cctgatagag ctcgcgaagc tcacatgcag     720

atgaaggctg cagcgctgcg aaacaccagt cgcagaatgt ttggtatgga cggcagtgtt     780

agtaacaagg aagaaaacac ggagagacac acagtggaag atgtcaatag agacatgcac     840

tctctcctgg gtatgcgcaa ctaa                                            864


<210> SEQ ID NO 18
<211> LENGTH: 287
<212> TYPE: PRT
<213> ORGANISM: PRSV-OA-CP

<400> SEQUENCE: 18

Ser Lys Asn Glu Ala Val Asp Ala Gly Leu Asn Glu Lys Phe Lys Glu
  1               5                  10                  15

Lys Glu Lys Gln Lys Glu Lys Glu Lys Glu Lys Gln Lys Glu Lys Glu
             20                  25                  30
```

-continued

```
Lys Asp Gly Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Thr
    50                  55                  60

Val Pro Arg Ile Lys Ser Phe Thr Asp Lys Met Ile Leu Pro Arg Ile
65                  70                  75                  80

Lys Gly Lys Ala Val Leu Asn Leu Asn His Leu Leu Gln Tyr Asn Pro
                85                  90                  95

Gln Gln Ile Asp Ile Ser Asn Thr Arg Ala Ala His Ser Gln Phe Glu
            100                 105                 110

Lys Trp Tyr Glu Gly Val Arg Asn Asp Tyr Ala Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

<210> SEQ ID NO 19
<211> LENGTH: 885
<212> TYPE: DNA
<213> ORGANISM: PRSV-VE-CP
<220> FEATURE:
<221> NAME/KEY: unsure
<222> LOCATION: (678)
<223> OTHER INFORMATION: M at position 678 in this sequence is either a or c

<400> SEQUENCE: 19

```
atggctgtgg atgctggttt gaatgggaag ctcaaagaaa aagagaaaaa agaaaaagaa     60

aaagaaaaac agaaagagaa agagaaagat gatgctagtg acggaaatga tgtgtcaact    120

agcacaaaaa ctggagagag agatagagat gtcaatattg ggaccagtgg aactttcact    180

gtccctagga ttaaatcatt tactgataag atgattttac cgagaattaa gggaaagact    240

gtccttaatt taaatcatct tcttcagtat aatccgaaac aaattgacat ttctaatact    300

cgtgccactc agtcgcaatt tgagaaatgg tatgagggag tgagggatga ttatggcctt    360

aatgataatg aaatgcaagt gatgctaaat ggcttgatgg tttggtgcat tgagaatggt    420

acatctccag acatatctgg tgtttgggtt atggtggatg gggaaaccca agttgattat    480

ccaatcaagc ctttaattga gcatgctaca ccgtcattta ggcaaattat ggctcatttt    540
```

-continued

```
agtaacgcgg cagaagcata cattgcgatg agaaatgcta ctgagaggta catgccgcgg    600

tatggaatca agagaaattt gactgacatc aacctagctc gatacgcttt tgatttctat    660

gaggtgaatt cgaaaacmcc tgatagggct cgtgaagctc acatgcagat gaaggctgca    720

gctttgcgaa acactaatcg cagaatgttt ggtatcgacg gcagtgttag caacaaggaa    780

gaaaacacgg agagacacac agtggatgat gtcaatagag acatgcactc tctcctgggt    840

atgcgcaact aaatactcgc acttgtgtgt ttgtcgagcc tgact                    885
```

<210> SEQ ID NO 20
<211> LENGTH: 282
<212> TYPE: PRT
<213> ORGANISM: PRSV-VE-CP
<220> FEATURE:
<221> NAME/KEY: UNSURE
<222> LOCATION: (225)
<223> OTHER INFORMATION: Xaa at position 225 in this sequence is any amino acid

<400> SEQUENCE: 20

```
Met Ala Val Asp Ala Gly Leu Asn Gly Lys Leu Lys Glu Lys Glu Lys
  1               5                  10                  15

Lys Glu Lys Glu Lys Glu Lys Gln Lys Glu Lys Glu Lys Asp Asp Ala
             20                  25                  30

Ser Asp Gly Asn Asp Val Ser Thr Ser Thr Lys Thr Gly Glu Arg Asp
         35                  40                  45

Arg Asp Val Asn Ile Thr Ser Gly Thr Phe Thr Val Pro Arg Ile Lys
     50                  55                  60

Ser Phe Thr Asp Lys Met Ile Leu Pro Arg Ile Lys Gly Lys Thr Val
 65                  70                  75                  80

Leu Asn Leu Asn His Leu Leu Gln Tyr Asn Pro Lys Gln Ile Asp Ile
                 85                  90                  95

Ser Asn Thr Arg Ala Thr Gln Ser Gln Phe Glu Lys Trp Tyr Glu Gly
            100                 105                 110

Val Arg Asp Asp Tyr Gly Leu Asn Asp Asn Glu Met Gln Val Met Leu
        115                 120                 125

Asn Gly Leu Met Val Trp Cys Ile Glu Asn Gly Thr Ser Pro Asp Ile
    130                 135                 140

Ser Gly Val Trp Val Met Val Asp Gly Glu Thr Gln Val Asp Tyr Pro
145                 150                 155                 160

Ile Lys Pro Leu Ile Glu His Ala Thr Pro Ser Phe Arg Gln Ile Met
                165                 170                 175

Ala His Phe Ser Asn Ala Ala Glu Ala Tyr Ile Ala Met Arg Asn Ala
            180                 185                 190

Thr Glu Arg Tyr Met Pro Arg Tyr Gly Ile Lys Arg Asn Leu Thr Asp
        195                 200                 205

Ile Asn Leu Ala Arg Tyr Ala Phe Asp Phe Tyr Glu Val Asn Ser Lys
    210                 215                 220

Xaa Pro Asp Arg Ala Arg Glu Ala His Met Gln Met Lys Ala Ala Ala
225                 230                 235                 240

Leu Arg Asn Thr Asn Arg Arg Met Phe Gly Ile Asp Gly Ser Val Ser
                245                 250                 255

Asn Lys Glu Glu Asn Thr Glu Arg His Thr Val Asp Asp Val Asn Arg
            260                 265                 270

Asp Met His Ser Leu Leu Gly Met Arg Asn
        275                 280
```

-continued

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 21
gagatctaga taatgatacc ggtctgaatg agaag 35

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 22
ggatctcgag agatcatctt atcagtaa 28

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 23
tagactcgag tgctggtttg aatgaaaaa 29

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 24
cgatcccggg gaatcaactt atcagtaa 28

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 25
tatacccggg tgctggtctt aatgagaag 29

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:
Amplification Oligos

<400> SEQUENCE: 26
ctacggatcc aaatcatctt gtcggtaa 28

-continued

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 27
tcaatctaga gtcgacgcta gatatgcttt cgac 34

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 28
aagtctcgag gtcgacccca ggagagagtg catg 34

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 29
aatacccggg gctagatatg ctttcgac 28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 30
ttatggatcc cctaggagag agtgcatg 28

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 31
agctaaccat ggaatcaagg agcactgatg attatc 36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 32
atttggatcc cggggttgcg catgcccagg agagag 36

<210> SEQ ID NO 33

-continued

```
<211> LENGTH: 36
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 33

agctaaccat ggaataatgg agcactgatg attatc                    36


<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 34

atttggatcc cggggttgcg catgcccagg agagag                    36


<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 35

cgatctagac cattggaata atgatccaag aatgaagc                  38


<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence:
      Amplification Oligos

<400> SEQUENCE: 36

cttaggatcc gttgcgcata cccaggagag a                         31
```

PAPAYA RINGSPOT VIRUS GENES

This application is a divisional of U.S. patent application Ser. No. 10/121,209, filed Apr. 11, 2002, now U.S. Pat. No. 7,078,586, issued Jul. 18, 2006, which application claims the benefit of U.S. Provisional Patent Application Ser. No. 60/283,007, filed Apr. 11, 2001, which are hereby incorporated by reference in their entirety.

FIELD OF THE INVENTION

The present invention relates to the isolation and purification of nucleic acid sequences encoding for papaya ringspot virus coat proteins, a method of conferring resistance to papaya ringspot virus by transforming plants with a construct containing one or more isolated viral coat protein nucleic acid sequences, and transgenic plants and seeds transformed with such multiple virus nucleic acid constructs.

BACKGROUND OF THE INVENTION

Papaya (*Carica papaya* L.) is an important fruit crop grown widely in tropical and subtropical lowland regions (Manshardt, "Papaya in Biotechnology of Perennial Fruit Crops," ed. *Hammerschlag,* 21:489-511, CAB Int., Wallingford, UK (1992)). Worldwide, Brazil, India, and Mexico are the largest producers of papaya. Hawaii, the largest producer of papaya in the United States, exports 66% of the total fresh production, primarily to the U.S. mainland and to Japan (Martin, "Papaya Production Statistics," *Proc. Annu. Hawaii Papaya Ind. Assoc. Conf., 39th, Kihei*, pp. 31-36, Sep. 23-24 (1994)). In total production, papaya ranks above strawberries and below grapefruit (Manshardt, "Papaya in Biotechnology of Perennial Fruit Crops," ed. *Hammerschlag,* 21:489-511, CAB Int., Wallingford, UK (1992)). The FAO estimated that about 5.7 million metric tons of fruit were harvested in 1995, almost double the 1980 harvest (Galinsky, "World Market for Papaya," *Reg. Agribus. Proj. Mark. Inf. Bull*. February No. 12, 5 pp. (1996)).

Papaya ringspot virus ("PRSV") is a member of the potyvirus group of plant viruses, which are pathogenic to several crop plants, and which exhibit cross-infectivity between members of different plant families. Generally, a potyvirus is a single-stranded (+) RNA plant virus. The viral genome is approximately 10,000 bases in length. The expression strategy of potyviruses includes translation of a complete polyprotein from the positive sense viral genomic RNA. PRSV is by far the most widespread and damaging virus that infects papaya, occurring worldwide wherever papaya is grown (Purcifull, "Papaya Ringspot Virus," *CMI/AAB Descr. Plant Viruses*, No. 292 (No. 84 Revis., July 1984) 8 pp. (1984)). PRSV infections have resulted in the devastation of the papaya industry in Brazil, Taiwan, and Hawaii in recent years (Gonsalves, D., "Control of Papaya Ringspot Virus in Papaya: A Case Study," *Annu. Rev. Phytopathol.* 36:415-37 (1998)). Various attempts have been made to control or prevent infection of crops by PRSV, but these have been largely unsuccessful.

The concept of parasite-derived resistance ("PDR"), conceived in the middle 1980s, offered a new approach for controlling PRSV (Sanford et al., "The Concept of Parasite-Derived Resistance—Deriving Resistance Genes from the Parasite's Own Genome," *J. Theor. Biol.* 113:395-405 (1985)). Parasite-derived resistance is a phenomenon whereby transgenic plants containing genes or sequences of a parasite are protected against detrimental effects of the same or related pathogens. The application of PDR for plant viruses was first demonstrated when transgenic tobacco expressing the coat protein gene of tobacco mosaic virus was protected against infection by tobacco mosaic virus (Powell-Abel et al., "Delay of Disease Development in Transgenic Plants that Express the Tobacco Mosaic Virus Coat Protein Gene," *Science,* 232:738-43 (1986)). Subsequent reports have shown that this approach is effective in controlling many plant viruses (Lomonossoff, G. P., "Pathogen-Derived Resistance to Plant Viruses," *Ann. Rev. Phytopathol.* 33:323-43 (1995)).

The vast majority of reports regarding PDR have utilized the coat protein genes of the viruses that are targeted for control. Although the testing of transgenic plants have been largely confined to laboratory and greenhouse experiments, a growing number of reports have shown that resistance is effective under field conditions (Grumet, R., "Development of Virus Resistant Plants via Genetic Engineering," *Plant Breeding Reviews* 12:47-49 (1994)). Two virus resistant crops have been deregulated by the Animal and Plant Heath Information Service of the United States Department of Agriculture ("USDA/APHIS") and, thus, are approved for unrestricted release into the environment in the U.S. Squash that are resistant to watermelon mosaic virus 2 and zucchini yellow mosaic potyviruses have been commercialized (Fuchs et al., "Resistance of Transgenic Hybrid Squash ZW-20 Expressing the Coat Protein Genes of Zucchini Yellow Mosaic Virus and Watermelon Mosaic Virus 2 to Mixed Infections by Both Potyviruses," *Bio/Technology* 13:1466-73 (1995); Tricoli, et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus," *Bio/Technology* 13:1458-65 (1995)). A transgenic Hawaiian papaya that is resistant to PRSV has also been developed (Fitch et al., "Virus Resistant Papaya Derived from Tissues Bombarded with the Coat Protein Gene of Papaya Ringspot Virus," *Bio/Technology* 10:1466-72 (1992); Tennant et al., "Differential Protection Against Papaya Ringspot Virus Isolates in Coat Protein Gene Transgenic Papaya and Classically Cross-Protected Papaya," *Phytopathology* 84:1359-66 (1994)). This resistant transgenic papaya was recently deregulated by USDA/APHIS. Deregulation of the transgenic papaya is timely, because Hawaii's papaya industry is being devastated by PRSV.

Remarkable progress has been made in developing virus resistant transgenic plants despite a poor understanding of the mechanisms involved in the various forms of pathogen-derived resistance (Lomonossoff, G. P., "Pathogen-Derived Resistance to Plant Viruses," *Ann. Rev. Phytopathol.* 33:323-43 (1995)). Although most reports deal with the use of coat protein genes to confer resistance, a growing number of reports have shown that genes encoding viral replicase (Golemboski et al., "Plants Transformed with a Tobacco Mosaic Virus Nonstructural Gene Sequence are Resistant to the Virus," *Proc. Natl. Acad. Sci. USA* 87:6311-15 (1990)), movement protein (Beck et al., "Disruption of Virus Movement Confers Broad-Spectrum Resistance Against Systemic Infection by Plant Viruses with a Triple Gene Block," *Proc. Natl. Acad. Sci. USA* 91:10310-14 (1994)), nuclear inclusion a-proteases ("NIa proteases") of potyviruses (Maiti et al., "Plants that Express a Potyvirus Proteinase Gene are Resistant to Virus Infection," *Proc. Natl. Acad. Sci. USA* 90:6110-14 (1993)), and other viral genes are also effective in conferring resistance. Furthermore, viral genes can be effective in the translatable and non-translatable sense forms, and, less frequently, antisense forms (Baulcombe, D. C., "Mechanisms of Pathogen-Derived Resistance to Viruses in Transgenic Plants," *Plant Cell* 8:1833-44 (1996); Dougherty et al., "Transgenes and Gene Suppression: Telling us Something New?" *Current Opinion in Cell Biology* 7:399-05 (1995); Lomonossoff, G. P., "Pathogen-Derived Resistance to Plant Viruses," *Ann. Rev. Phytopathol.* 33:323-43 (1995)).

Notwithstanding the progress made in the field of plant resistance to viral pathogens, PRSV continues to exert its devastating effect upon papaya and other crops the world over. While the transgenic Hawaiian papaya is controlling the problem temporarily in Hawaii, that line unfortunately appears to susceptible to PRSV isolates with origins outside Hawaii. These observations suggest that transgenic papaya with coat protein genes specific to targeted PRSV isolates would need to be developed for transgenic papaya to effectively control PRSV worldwide. A more practical and comprehensive approach is needed to halt the devastation of PRSV. Such an approach would impart resistance to PRSV by utilizing genetic engineering techniques to provide greater and more reliable multi-pathogen resistance to crops to PRSV and other RNA-viral plant pathogens.

The present invention is directed to overcoming these and other deficiencies in the art.

SUMMARY OF THE INVENTION

The present invention relates to isolated nucleic acid molecules encoding a viral coat protein of papaya ringspot virus and the protein encoded by those nucleic acid molecules.

Another aspect of the present invention pertains to nucleic acid constructs containing the isolated nucleic acid molecules of the present invention operably linked to 5' and 3' regulatory regions.

The present invention also relates to nucleic acid constructs containing a plurality of trait DNA molecules, wherein at least some of the plurality of trait DNA molecules have a length that is insufficient to independently impart that trait to plants transformed with that trait DNA molecule. However, the plurality of trait DNA molecules are capable of collectively imparting their traits to plants transformed with the DNA construct and thereby effecting the silencing of the DNA construct. The trait associated with the DNA molecules of this construct is disease resistance, and the trait DNA molecules are derived from a gene encoding a papaya ringspot virus coat protein in a papaya ringspot virus strain selected from the group consisting of Thailand ("TH"), Keaau ("KE"), Kapoho ("KA"), Mexico ("ME"), Taiwan ("YK"), Brazil ("BR"), Jamaica ("JA"), Oahu ("OA"), and Panaewa ("PA").

The present invention also relates to a DNA construct containing a fusion gene which includes a trait DNA molecule which has a length insufficient to independently impart a desired trait to plants transformed with the trait molecule, operatively coupled to a silencer molecule effective to achieve post-transcriptional gene silencing. The trait DNA molecule and the silencer molecule collectively impart the trait to plants transformed with the construct. The DNA molecules of this DNA construct are derived from a gene encoding a papaya ringspot viral coat protein from a papaya ringspot virus strain selected from the group consisting of TH, KE, KA, ME, YK, BR, JA, OA, and VE.

The present invention also relates to host cells, plant cells, transgenic plants, and transgenic plant seeds containing the nucleic acid constructs of the present invention.

The present invention also relates to a method of imparting resistance against papaya ringspot virus to papaya plants. This involves transforming a papaya plant with the constructs of the present invention.

BRIEF DESCRIPTION OF THE DRAWINGS

FIG. 1A shows the expression cassette, pEPJ-YKT, containing the PRSV-CP variable regions of the YK, KE, and TH strains ligated into the pEPJ vector. FIG. 1B shows the transformation vector pGA482G.

FIG. 2A shows the pNP-YKT vector, containing the silencer DNA molecule (M1/2NP) and the PRSV-CP variable regions of PRSV strains YK, KE, and TH. FIG. 2B shows the pGFP-YKT vector, containing the silencer molecule GFP ligated to the PRSV-CP variable regions of PRSV strains YK, KE, and TH PRSV strains.

FIG. 3A shows clone pNP-K; FIG. 3B shows clone pNP-KK; FIG. 3C shows clone pNP-EE; FIG. 3D shows clone pNP-KKTC; FIG. 3E shows clone pNP-KKTV; FIG. 3F shows clone pNP-EETC, and FIG. 3G shows clone pNP-EETV.

DETAILED DESCRIPTION

Figure 1:
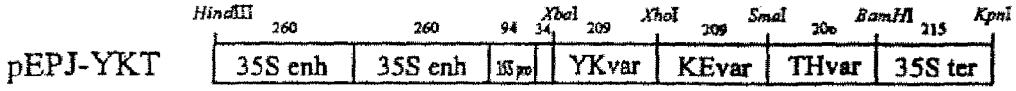
FIGS. 1A-B show the cloning vectors used for the DNA constructs of the present invention.
Figure 1:
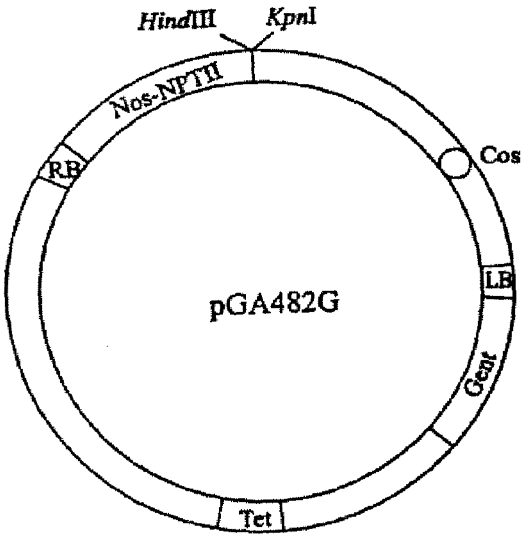

The present invention relates to nucleic acids which encode for a viral coat protein ("CP") of papaya ringspot virus ("PRSV").

One suitable form of the nucleic acid of the present invention is the CP gene isolated from the PRSV strain Kapoho ("KA"), which has a nucleic acid sequence corresponding to SEQ ID NO: 1 as follows:

```
tccaagaatg aagctgtgga tgctggtttg aatgaaaaac tcaaagagaa agaaagacag  60
aaagaaaaag aaaaagaaaa acaaaaagaa aaaggaaaag acgatgctag tgacgaaaat 120
gatgtgtcaa ctagcacaaa aactggagag agagatagag atgtcaatgt tgggaccagt 180
ggaactttcg ctgttccgag aattaaatca tttactgata agttgattct accaagaatt 240
aagggaaaga ctgtccttaa tttaagtcat cttcttcagt ataatccgca acaaattgac 300
atttctaaca ctcgtgccac tcagtcacaa tttgagaagt ggtatgaggg agtgagggat 360
```

-continued

```
gattatggcc ttaatgataa tgaaatgcaa gttatgctaa atggtttgat ggtttggtgt 420

atcgagaatg gtacatctcc agacatatct ggtgtatggg ttatgatgga tggggaaacc 480

caagttgatt atccaaccaa gcctttaatt gagcatgata ctccgtcatt taggcaaatt 540

atggctcact ttagtaacgc ggcagaagca tacattgcga agagaaatgc tactgagagg 600

tacatgccgc ggtacggaat caagagaaat ttgactgaca ttagcctcgc tagatatgct 660

ttcgacttct atgaggtgaa ttcgaaaaca cctgataggg ctcgcgaagc ccacatgcag 720

atgaaggctg cagcgctgcg aaacactagt cgcagaatgt ttggtatgga cggcagtgtt 780

agtaacaagg aagaaaacac ggagagacac acagtggaag atgtcgatag agacatgcac 840

tctctcctgg gtatgcgcaa ctaa                                        864
```

The present invention also relates to the PRSV-KA-CP, encoded by the nucleotide corresponding to SEQ ID NO: 1, where the protein encoded has an amino acid sequence corresponding to SEQ ID NO: 2, as follows:

```
Ser Lys Asn Glu Ala Val Asp Ala Gly Leu Asn Glu Lys Leu Lys Glu
 1               5                  10                  15

Lys Glu Arg Gln Lys Glu Lys Glu Lys Glu Lys Gln Lys Glu Lys Gly
            20                  25                  30

Lys Asp Asp Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Ala
    50                  55                  60

Val Pro Arg Ile Lys Ser Phe Thr Asp Lys Leu Ile Leu Pro Arg Ile
65                  70                  75                  80

Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Asp Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asp Arg Asp Met His Ser Leu Leu Gly Met Arg Asn
        275                 280                 285
```

The present invention also relates to an isolated nucleic acid molecule encoding a CP gene isolated from the Thailand ("TH") strain of PRSV, which has a nucleic acid sequence corresponding to SEQ ID NO: 3 as follows:

```
tccaagaatg aagctgtgga tgctggtctt aatgagaagt tcaaagataa agaaaaacag  60
aaagaagaaa aagataaaca aaaaggtaaa gaaaataatg aagctagtga cggaaatgat 120
gtgtcaacta gcacaaaaac tggagagaga gatagagatg tcaatgccgg aactagtggt 180
actttcactg ttccgagaat aaaattattt accgacaaga tgattttacc aagaattaag 240
ggaaaaactg tccttagttt aaatcatctt cttcagtata atccgcaaca aatagacatc 300
tcaaacactc gtgccactca atctcaattc gaaaagtggt atgagggagt gaggaatgat 360
tacggtctta atgataacga aatgcaagtg atgttaaatg gtttgatggt ttggtgcatc 420
gaaaatggaa catccccaga catatctggt gtctgggtga tgatggatgg ggaaacccaa 480
gtcgattatc ccatcaagcc tttgatcgaa catgcaactc cttcgttcag gcaaatcatg 540
gctcacttca gtaacgcggc agaggcatac atcgcaaaga ggaatgctac tgagaggtac 600
atgccgcggt atggaatcaa gaggaatctg actgacatta gtctcgctag atatgctttc 660
gacttctatg aggtgaactc aaaaacacct gatagggctc gtgaagctca tatgcagatg 720
aaggctgcag cgctgcgcaa cactgatcgc agaatgtttg gaatggacgg cagtgtcagt 780
aacaaggaag aaaacacgga gagacacaca gtggaagatg tcaacagaga catgcactct 840
ctcctaggta tgcgcaattg a                                          861
```

The present invention also relates to the viral coat protein of the TH strain of PRSV, encoded for by SEQ ID NO: 3, which corresponds to amino acid SEQ ID NO: 4, as follows:

```
Ser Lys Asn Glu Ala Val Asp Ala Gly Leu Asn Glu Lys Phe Lys Asp
1               5                   10                  15

Lys Glu Lys Gln Lys Glu Glu Lys Asp Lys Gln Lys Gly Lys Glu Asn
            20                  25                  30

Asn Glu Ala Ser Asp Gly Asn Asp Val Ser Thr Ser Thr Lys Thr Gly
        35                  40                  45

Glu Arg Asp Arg Asp Val Asn Ala Gly Thr Ser Gly Thr Phe Thr Val
    50                  55                  60

Pro Arg Ile Lys Leu Phe Thr Asp Lys Met Ile Leu Pro Arg Ile Lys
65                  70                  75                  80

Gly Lys Thr Val Leu Ser Leu Asn His Leu Leu Gln Tyr Asn Pro Gln
                85                  90                  95

Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Val Met Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Ala
            180                 185                 190

Lys Arg Asn Ala Thr Glu Arg Tyr Met Pro Arg Tyr Gly Ile Lys Arg
        195                 200                 205
```

-continued

```
Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asp Arg Arg Met Phe Gly Met Asp
                245                 250                 255

Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285
```

Also suitable as a nucleic acid for use in the present invention is the nucleic acid which encodes a CP gene isolated from the Keaau ("KE") strain of PRSV. PRSV-KE contains two "cut-sites", i.e., two potential cleavage sites for a mature coat protein. The first cleavage site sequence in the KE strain of PRSV, identified herein as KE-CP1, corresponds to SEQ ID NO: 5 (KECP1) as follows:

```
tcaaggagca ctgatgatta tcaacttgtt tggagtgaca atacacatgt gtttcatcag   60
tccaagaatg aagctgtgga tgctggtttg aatgaaaaac tcaaagagaa agaaaaacag 120
aaagaaaaag aaaaagaaaa acaaaaagaa aaaggaagag acgatgctag tgacgaaaat 180
gatgtgtcaa ctagcacaaa aactggagag agagatagag atgtcaatgt tgggaccagt 240
ggaactttcg ctgttccgag aattaaatca tttactgata agttgattct accaagaatt 300
aagggaaaga ctgtccttaa tttaagtcat cttcttcagt ataatccgca acaaattgac 360
atttctaaca ctcgtgccac tcagtcacaa tttgagaagt ggtatgaggg agtgagggat 420
gattatggcc ttaatgataa tgaaatgcaa gttatgctaa atggtttgat ggtttggtgt 480
atcgagaatg gtacatctcc agacatatct ggtgtatggg ttatgatgga tggggaaacc 540
caagttgatt atccaaccaa gcctttaatt gagcatgcta ctccgtcatt taggcaaatt 600
atggctcact ttagtaacgc ggcagaagca tacattgcga agagaaatgc tactgagagg 660
tacatgccgc ggtacggaat caagagaaat ttgactgacg ttagcctcgc tagatatgct 720
ttcgacttct atgaggtgaa ttcgaaaaca cctgataggg ctcgcgaagc ccacatgcag 780
atgaaggctg cagcgctgcg aaacactagt cgcagaatgt ttggtatgga cggcagtgtt 840
agtaacaagg aagaaaacac ggagagacac acagtggaag atgtcaatag agacatgcac 900
tctctcctgg gcatgcgcaa c                                           921
```

A second nucleotide sequence encoding a PRSV-KE coat protein sequence, which starts from the second KE-CP cleavage site, is identified as KE-CP2 herein, and corresponds to SEQ ID NO: 6, as follows:

```
tccaagaatg aagctgtgga tgctggtttg aatgaaaaac tcaaagagaa agaaaaacag   60
aaagaaaaag aaaaagaaaa acaaaaagaa aaaggaaaag acgatgctag tgacgaaaat 120
gatgtgtcaa ctagcacaaa aactggagag agagatagag atgtcaatgt tgggaccagt 180
ggaactttcg ctgttccgag aattaaatca tttactgata agttgattct accaagaatt 240
aagggaaaga ctgtccttaa tttaagtcat cttcttcagt ataatccgca acaaattgac 300
atttctaaca ctcgtgccac tcagtcacaa tttgagaagt ggtatgaggg agtgagggat 360
gattatggcc ttaatgataa tgaaatgcaa gttatgctaa atggtttgat ggtttggtgt 420
atcgagaatg gtacatctcc agacatatct ggtgtatggg ttatgatgga tggggaaacc 480
caagttgatt atccaaccaa gcctttaatt gagcatgcta ctccgtcatt taggcaaatt 540
```

-continued

```
atggctcact ttagtaacgc ggcagaagca tacattgcga agagaaatgc tactgagagg 600

tacatgccgc ggtacggaat caagagaaat ttgactgacg ttagcctcgc tagatatgct 660

ttcgacttct atgaggtgaa ttcgaaaaca cctgataggg ctcgcgaagc ccacatgcag 720

atgaaggctg cagcgctgcg aaacactagt cgcagaatgt ttggtatgga cggcagtgtt 780

agtaacaagg aagaaaacac ggagagacac acagtggaag atgtcaatag agacatgcac 840

tctctcctgg gcatgcgcaa ctaa                                        864
```

SEQ ID NOS: 5 and 6 contain, respectively, the N terminus and C terminus cleavage sites for PRSV-KE coat protein. Both cleavage sites result in proteins that appear to be functional in viral replication in the plant. SEQ ID NO: 5 encodes the first coat protein cleavage site product, CP1, of the KE strain of PRSV. KE-CP1 has an amino acid sequence corresponding to SEQ ID NO: 7, as follows:

```
Ser Arg Ser Thr Asp Asp Tyr Gln Leu Val Trp Ser Asp Asn Thr His
1               5                   10                  15

Val Phe His Gln Ser Lys Asn Glu Ala Val Asp Ala Gly Leu Asn Glu
            20                  25                  30

Lys Leu Lys Glu Lys Glu Lys Gln Lys Glu Lys Glu Lys Glu Lys Gln
        35                  40                  45

Lys Glu Lys Gly Arg Asp Asp Ala Ser Asp Glu Asn Asp Val Ser Thr
    50                  55                  60

Ser Thr Lys Thr Gly Glu Arg Asp Arg Asp Val Asn Val Gly Thr Ser
65                  70                  75                  80

Gly Thr Phe Ala Val Pro Arg Ile Lys Ser Phe Thr Asp Lys Leu Ile
                85                  90                  95

Leu Pro Arg Ile Lys Gly Lys Thr Val Leu Asn Leu Ser His Leu Leu
            100                 105                 110

Gln Tyr Asn Pro Gln Gln Ile Asp Ile Ser Asn Thr Arg Ala Thr Gln
        115                 120                 125

Ser Gln Phe Glu Lys Trp Tyr Glu Gly Val Arg Asp Asp Tyr Gly Leu
    130                 135                 140

Asn Asp Asn Glu Met Gln Val Met Leu Asn Gly Leu Met Val Trp Cys
145                 150                 155                 160

Ile Glu Asn Gly Thr Ser Pro Asp Ile Ser Gly Val Trp Val Met Met
                165                 170                 175

Asp Gly Glu Thr Gln Val Asp Tyr Pro Thr Lys Pro Leu Ile Glu His
            180                 185                 190

Ala Thr Pro Ser Phe Arg Gln Ile Met Ala His Phe Ser Asn Ala Ala
        195                 200                 205

Glu Ala Tyr Ile Ala Lys Arg Asn Ala Thr Glu Arg Tyr Met Pro Arg
    210                 215                 220

Tyr Gly Ile Lys Arg Asn Leu Thr Asp Val Ser Leu Ala Arg Tyr Ala
225                 230                 235                 240

Phe Asp Phe Tyr Glu Val Asn Ser Lys Thr Pro Asp Arg Ala Arg Glu
                245                 250                 255

Ala His Met Gln Met Lys Ala Ala Ala Leu Arg Asn Thr Ser Arg Arg
            260                 265                 270

Met Phe Gly Met Asp Gly Ser Val Ser Asn Lys Glu Glu Asn Thr Glu
        275                 280                 285

Arg His Thr Val Glu Asp Val Asn Arg Asp Met His Ser Leu Leu Gly
    290                 295                 300

Met Arg Asn
305
```

SEQ ID NO: 6 encodes the second coat protein cleavage site product, CP2, of the KE strain of PRSV. KE-CP2 has an amino acid sequence corresponding to SEQ ID NO: 8, as follows:

```
Ser Lys Asn Glu Ala Val Asp Ala Gly Leu Asn Glu Lys Leu Lys Glu
 1               5                  10                  15

Lys Glu Lys Gln Lys Glu Lys Glu Lys Glu Lys Gln Lys Glu Lys Gly
            20                  25                  30

Lys Asp Asp Ala Ser Asp Glu Asn Asp Val Ser Thr Ser Thr Lys Thr
        35                  40                  45

Gly Glu Arg Asp Arg Asp Val Asn Val Gly Thr Ser Gly Thr Phe Ala
    50                  55                  60

Val Pro Arg Ile Lys Ser Phe Thr Asp Lys Leu Ile Leu Pro Arg Ile
65                  70                  75                      80

Lys Gly Lys Thr Val Leu Asn Leu Ser His Leu Leu Gln Tyr Asn Pro
                85                  90                  95

Gln Gln Ile Asp Ile Ser Asn Thr Arg Ala Thr Gln Ser Gln Phe Glu
            100                 105                 110

Lys Trp Tyr Glu Gly Val Arg Asp Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Thr Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Val Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

Another nucleic acid suitable in the present invention is the CP gene isolated from the Taiwan ("YK") strain of PRSV, corresponding to SEQ ID NO: 9, as follows:

```
tctaaaaatg aagctgtgga taccggtctg aatgagaagc tcaaagaaaa agaaaagcag  60
aaagaaaaag aaaaagataa acaacaagat aaagacaatg atggagctag tgacggaaac 120
gatgtgtcaa ctagcacaaa aactggagag agagataggg atgtcaatgc cggaactagt 180
ggaaccttca ctgttccgag gataaagtca tttactgata agatgatctt accaagaatt 240
aagggaaaaa ctgtccttaa tttaaatcat cttcttcagt ataatccgaa acaagttgac 300
atctcaaaca ctcgcgccac tcaatctcaa tttgagaagt ggtatgaggg agtgagaaat 360
gattatggcc ttaatgataa cgaaatgcaa gtaatgttaa atggtttgat ggtttggtgt 420
atcgaaaatg gtacatctcc agatatatct ggtgtctggg ttatgatgga tggggaaacc 480
```

-continued

```
caagtcgatt atcccattaa acctttgatt gaacacgcaa ctccttcatt taggcaaatc 540

atggctcact tcagtaacgc ggcagaggca tacatcgcga agaggaatgc aactgagaag 600

tacatgccgc ggtatggaat caagagaaat ttgactgaca ttagtctcgc tagatatgct 660

ttcgatttct atgaggtgaa ttcgaaaaca cctgataggg ctcgtgaagc tcatatgcag 720

atgaaggctg cagcgctacg caatactaat cgcaaaatgt ttggaatgga cggcagtgtc 780

agtaacaagg aagaaaacac ggagagacac acagtggaag atgtcaacag agacatgcac 840

tctctcctgg gtatgcgcaa ttga                                        864
```

SEQ ID NO: 9 encodes the CP of the YK strain of PRSV which has an amino acid sequence corresponding to SEQ ID NO: 10, as follows:

```
Ser Lys Asn Glu Ala Val Asp Thr Gly Leu Asn Glu Lys Leu Lys Glu
  1               5                  10                  15

Lys Glu Lys Gln Lys Glu Lys Glu Lys Asp Lys Gln Gln Asp Lys Asp
             20                  25                  30

Asn Asp Gly Ala Ser Asp Gly Asn Asp Val Ser Thr Ser Thr Lys Thr
         35                  40                  45

Gly Glu Arg Asp Arg Asp Val Asn Ala Gly Thr Ser Gly Thr Phe Thr
     50                  55                  60

Val Pro Arg Ile Lys Ser Phe Thr Asp Lys Met Ile Leu Pro Arg Ile
 65                  70                  75                  80

Lys Gly Lys Thr Val Leu Asn Leu Asn His Leu Leu Gln Tyr Asn Pro
                 85                  90                  95

Lys Gln Val Asp Ile Ser Asn Thr Arg Ala Thr Gln Ser Gln Phe Glu
            100                 105                 110

Lys Trp Tyr Glu Gly Val Arg Asn Asp Tyr Gly Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Lys Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Lys Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

Another nucleic acid suitable in the present invention is the CP gene isolated from the Mexico ("ME") strain of PRSV, corresponding to SEQ ID NO: 11, as follows:

```
tccaagaatg aagctgtgga tgctggtttg aatgaaaaac tcaaagaaaa agaaaaacag  60

aaagaaaaag aaaaacaaaa agaaaaagaa aaagacaatg ctagtgacgg aaatgatgtg 120

tcgactagca caaaaactgg agagaaagat agagatgtca atgtcggaac tagtggaact 180

ttcactgttc cgagaattaa atcatttact gataagatga ttctaccgag aattaaggga 240

aagactgtcc ttaatttaaa tcatcttctt cagtataatc cgcaacaaat tgatatttct 300

aacactcgtg ccactcagtc acaatttgag aaatggtatg agggagtgag gaatgattat 360

ggtctgaatg ataatgaaat gcaagtgatg ctgaatggct tgatggtttg gtgtatcgag 420

aatggtacat ctccagacat atctggtgtt tgggttatga tggatgggga aattcaagtt 480

gactatccaa tcaagcctct aattgagcat gctaccccgt catttaggca gattatggct 540

cactttagta acgcggcaga agcatatatt gcaaagagaa atgccactga gaggtacatg 600

ccgcggtatg gaatcaagag aaatttgact gacattagcc tcgctaggta cgctttcgat 660

ttctatgagg ttaattcgaa aacacctgat agggctcgcg aagctcacat gcagatgaaa 720

gctgcagcgc tgcgaaacac tagtcgcaga atgtttggta tgggcggcag tgttagtaac 780

aaggaagaaa acacggaaag acacacagtg gaagatgtca atagagacat gcactctctc 840

ctgggtatgc gcaac                                                 855
```

SEQ ID NO: 11 encodes the CP of the ME strain of PRSV which has an amino acid sequence corresponding to SEQ ID NO: 12, as follows:

```
Ser Lys Asn Glu Ala Val Asp Ala Gly Leu Asn Glu Lys Leu Lys Glu
  1               5                  10                  15

Lys Glu Lys Gln Lys Glu Lys Glu Lys Gln Lys Glu Lys Glu Lys Asp
             20                  25                  30

Asn Ala Ser Asp Gly Asn Asp Val Ser Thr Ser Thr Lys Thr Gly Glu
         35                  40                  45

Lys Asp Arg Asp Val Asn Val Gly Thr Ser Gly Thr Phe Thr Val Pro
     50                  55                  60

Arg Ile Lys Ser Phe Thr Asp Lys Met Ile Leu Pro Arg Ile Lys Gly
 65                  70                  75                  80

Lys Thr Val Leu Asn Leu Asn His Leu Leu Gln Tyr Asn Pro Gln Gln
                 85                  90                  95

Ile Asp Ile Ser Asn Thr Arg Ala Thr Gln Ser Gln Phe Glu Lys Trp
            100                 105                 110

Tyr Glu Gly Val Arg Asn Asp Tyr Gly Leu Asn Asp Asn Glu Met Gln
        115                 120                 125

Val Met Leu Asn Gly Leu Met Val Trp Cys Ile Glu Asn Gly Thr Ser
    130                 135                 140

Pro Asp Ile Ser Gly Val Trp Val Met Met Asp Gly Glu Ile Gln Val
145                 150                 155                 160

Asp Tyr Pro Ile Lys Pro Leu Ile Glu His Ala Thr Pro Ser Phe Arg
                165                 170                 175

Gln Ile Met Ala His Phe Ser Asn Ala Ala Glu Ala Tyr Ile Ala Lys
            180                 185                 190

Arg Asn Ala Thr Glu Arg Tyr Met Pro Arg Tyr Gly Ile Lys Arg Asn
```

-continued

```
        195                 200                 205

Leu Thr Asp Ile Ser Leu Ala Arg Tyr Ala Phe Asp Phe Tyr Glu Val
    210                 215                 220

Asn Ser Lys Thr Pro Asp Arg Ala Arg Glu Ala His Met Gln Met Lys
225                 230                 235                 240

Ala Ala Ala Leu Arg Asn Thr Ser Arg Arg Met Phe Gly Met Gly Gly
                245                 250                 255

Ser Val Ser Asn Lys Glu Glu Asn Thr Glu Arg His Thr Val Glu Asp
            260                 265                 270

Val Asn Arg Asp Met His Ser Leu Leu Gly Met Arg Asn
        275                 280                 285
```

Another nucleic acid suitable in the present invention is the CP gene isolated from the Brazil ("BR") strain of PRSV, corresponding to SEQ ID NO: 13, as follows:

```
tccaaaaatg aagctgtgga tgctggtttg aatgaaaagc gtaaagaaca agagaaacaa  60
gaagaaaaag aagaaaaaca aaaaaagaaa gaaaaagacg atgctagtta cggaaacgat 120
gtgtcaacta gcacaagaac tggagagaga gacagagatg tcaatgttgg gaccagtgga 180
actttcactg ttccgagaac aaaatcattt actgataaga tgattttacc tagaattaag 240
ggaaaaactg tccttaattt aaatcatctg attcagtata atccgcaaca aattgacatt 300
tctaacactc gtgctactca atcacaattt gagaagtggt acgagggagt gaggaatgat 360
tatggcctta atgataatga gatgcaaata gtgctaaatg gtttgatggt ttggtgtatc 420
gaaaacggta catctccaga catatctggt gtctgggtta tgatggatgg ggaaacccag 480
gttgactatc caatcaagcc tttaattgag catgctactc cgtcgtttag gcaaattatg 540
gctcatttca gtaacgcggc agaagcatac attacaaaga gaaatgctac tgagaggtac 600
atgccgcggt atgggatcaa gagaaatttg actgacatta gtcttgctag atatgctttc 660
gatttctatg aggtgaattc gaaaacacct gatagggctc gcgaagctca catgcagatg 720
aaagctgcag cgctgcgaaa cactaatcgc agaatgtttg gtatggacgg cagtgttagt 780
aacaaggaag aaaacacgga gagacacaca gtggaagatg tcaatagaga catgcactct 840
ctcctgggta tgcgcaactg a                                           861
```

SEQ ID NO: 13 encodes the CP of the BR strain of PRSV which has an amino acid sequence corresponding to SEQ ID NO: 14, as follows:

```
Ser Lys Asn Glu Ala Val Asp Ala Gly Leu Asn Glu Lys Arg Lys Glu
  1               5                  10                  15

Gln Glu Lys Gln Glu Glu Lys Glu Glu Lys Gln Lys Lys Lys Glu Lys
             20                  25                  30

Asp Asp Ala Ser Tyr Gly Asn Asp Val Ser Thr Ser Thr Arg Thr Gly
         35                  40                  45

Glu Arg Asp Arg Asp Val Asn Val Gly Thr Ser Gly Thr Phe Thr Val
     50                  55                  60

Pro Arg Thr Lys Ser Phe Thr Asp Lys Met Ile Leu Pro Arg Ile Lys
 65                  70                  75                  80

Gly Lys Thr Val Leu Asn Leu Asn His Leu Ile Gln Tyr Asn Pro Gln
                 85                  90                  95
```

-continued

```
Gln Ile Asp Ile Ser Asn Thr Arg Ala Thr Gln Ser Gln Phe Glu Lys
            100                 105                 110

Trp Tyr Glu Gly Val Arg Asn Asp Tyr Gly Leu Asn Asp Asn Glu Met
        115                 120                 125

Gln Ile Val Leu Asn Gly Leu Met Val Trp Cys Ile Glu Asn Gly Thr
    130                 135                 140

Ser Pro Asp Ile Ser Gly Val Trp Val Met Met Asp Gly Glu Thr Gln
145                 150                 155                 160

Val Asp Tyr Pro Ile Lys Pro Leu Ile Glu His Ala Thr Pro Ser Phe
                165                 170                 175

Arg Gln Ile Met Ala His Phe Ser Asn Ala Ala Glu Ala Tyr Ile Thr
            180                 185                 190

Lys Arg Asn Ala Thr Glu Arg Tyr Met Pro Arg Tyr Gly Ile Lys Arg
        195                 200                 205

Asn Leu Thr Asp Ile Ser Leu Ala Arg Tyr Ala Phe Asp Phe Tyr Glu
    210                 215                 220

Val Asn Ser Lys Thr Pro Asp Arg Ala Arg Glu Ala His Met Gln Met
225                 230                 235                 240

Lys Ala Ala Ala Leu Arg Asn Thr Asn Arg Arg Met Phe Gly Met Asp
                245                 250                 255

Gly Ser Val Ser Asn Lys Glu Glu Asn Thr Glu Arg His Thr Val Glu
            260                 265                 270

Asp Val Asn Arg Asp Met His Ser Leu Leu Gly Met Arg Asn
        275                 280                 285
```

Another nucleic acid suitable in the present invention is a CP gene isolated from the Jamaica ("JA") strain of PRSV, corresponding to SEQ ID NO: 15, as follows:

```
tctaaaaatg aagctgtgga tgctggttta aatgaaaagc tcaaagaaaa agaaaaacag   60

aaagataaag aaaaagaaaa acaaaaagat aaagaaaaag gagatgctag tgacggaaat  120

gatggttcga ctagcacaaa aactggagag agagatagag atgtcaatgt tgggaccagt  180

ggaacttcca ctgttccgag aattaaatca ttcactgata agatggttct accaagaatt  240

aagggaaaaa ctgtccttaa tttaaatcat cttcttcagt ataatccaca acaaattgac  300

atttctaaca ctcgtgccac tcagtcacaa tttgagaagt ggtacgaagg agtgaggagt  360

gattatggcc taaatgatag tgaaatgcaa gtgacgctaa atggcttgat ggtttggtgt  420

atcgagaatg gtacatctcc agacatatct ggtgtctggg ttatgatgga tggggaaacc  480

caagttgatt atccaatcaa gcctttaatt gagcacgcta ccccatcatt taggcagatt  540

atggctcact tcagtaacgc ggcagaagca tacactgcaa agagaaatgc tactgagagg  600

tacatgccgc ggtatggaat caagagaaat ttgactgaca ttagtctcgc tagatacgct  660

ttcgatttct atgaggtgaa ttcgaagaca cctgataggg ctcgtgaagc tcacatgcag  720

atgaaagctg cagcgctgcg aaacactaat cgcagaatgt ttggtatgga cggcagtgtt  780

agtaacaatg aagaaaacac ggagagacac acagtggaag atgtctatat agacatgcac  840

tctctcctgc gtttgcgcaa ctga                                          864
```

SEQ ID NO: 15 encodes the CP of the JA strain of PRSV which has an amino acid sequence corresponding to SEQ ID NO: 16, as follows:

```
Ser Lys Asn Glu Ala Val Asp Ala Gly Leu Asn Glu Lys Leu Lys Glu
  1               5                  10                  15

Lys Glu Lys Gln Lys Asp Lys Glu Lys Glu Lys Gln Lys Asp Lys Glu
             20                  25                  30

Lys Gly Asp Ala Ser Asp Gly Asn Asp Gly Ser Thr Ser Thr Lys Thr
         35                  40                  45

Gly Glu Arg Asp Arg Asp Val Asn Val Gly Thr Ser Gly Thr Ser Thr
     50                  55                  60

Val Pro Arg Ile Lys Ser Phe Thr Asp Lys Met Val Leu Pro Arg Ile
 65                  70                  75                  80

Lys Gly Lys Thr Val Leu Asn Leu Asn His Leu Leu Gln Tyr Asn Pro
                 85                  90                  95

Gln Gln Ile Asp Ile Ser Asn Thr Arg Ala Thr Gln Ser Gln Phe Glu
            100                 105                 110

Lys Trp Tyr Glu Gly Val Arg Ser Asp Tyr Gly Leu Asn Asp Ser Glu
        115                 120                 125

Met Gln Val Thr Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Thr
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Asn Arg Arg Met Phe Gly Met
                245                 250                 255

Asp Gly Ser Val Ser Asn Asn Glu Glu Asn Thr Glu Arg His Thr Val
            260                 265                 270

Glu Asp Val Tyr Ile Asp Met His Ser Leu Leu Arg Leu Arg Asn
        275                 280                 285
```

Another nucleic acid suitable in the present invention is a CP gene isolated from the Oahu ("OA") strain of PRSV, corresponding to SEQ ID NO: 17, as follows:

```
tccaagaatg aagctgtgga tgctggtttg aatgaaaaat tcaaagagaa ggaaaaacag   60

aaagaaaaag aaaaagaaaa acaaaaagag aaagaaaaag atggtgctag tgacgaaaat 120

gatgtgtcaa ctagcacaaa aactggagag agagatagag atgtcaatgt cgggaccagt 180

ggaactttca cagttccgag aattaaatca tttactgata agatgattct accgagaatt 240

aaggggaagg ctgtccttaa tttaaatcat cttcttcagt acaatccgca acaaatcgac 300

atttctaaca ctcgtgccgc tcattcacaa tttgaaaagt ggtatgaggg agtgaggaat 360

gattatgccc ttaatgataa tgaaatgcaa gtgatgctaa atggtttgat ggtttggtgt 420
```

-continued

```
atcgagaatg gtacatctcc agacatatct ggtgtctggg taatgatgga tggggaaacc 480

caagtcgatt atccaatcaa gcctttgatt gagcatgcta ctccgtcatt taggcaaatt 540

atggctcact ttagtaacgc ggcagaagca tacattgcga agagaaatgc tactgagagg 600

tacatgccgc ggtatggaat caagagaaat ttgactgaca ttagcctcgc tagatacgct 660

ttcgactttt atgaggtgaa ttcgaaaaca cctgatagag ctcgcgaagc tcacatgcag 720

atgaaggctg cagcgctgcg aaacaccagt cgcagaatgt ttggtatgga cggcagtgtt 780

agtaacaagg aagaaaacac ggagagacac acagtggaag atgtcaatag agacatgcac 840

tctctcctgg gtatgcgcaa ctaa                                        864
```

SEQ ID NO: 17 encodes the CP of the OA strain of PRSV which has an amino acid sequence corresponding to SEQ ID NO: 18, as follows:

```
Ser Lys Asn Glu Ala Val Asp Ala Gly Leu Asn Glu Lys Phe Lys Glu
  1               5                  10                  15

Lys Glu Lys Gln Lys Glu Lys Glu Lys Glu Lys Gln Lys Glu Lys Glu
             20                  25                  30

Lys Asp Gly Ala Ser Asp Glu Asn Asp Val Ser Thr Ser Thr Lys Thr
         35                  40                  45

Gly Glu Arg Asp Arg Asp Val Asn Val Gly Thr Ser Gly Thr Phe Thr
     50                  55                  60

Val Pro Arg Ile Lys Ser Phe Thr Asp Lys Met Ile Leu Pro Arg Ile
 65                  70                  75                  80

Lys Gly Lys Ala Val Leu Asn Leu Asn His Leu Leu Gln Tyr Asn Pro
                 85                  90                  95

Gln Gln Ile Asp Ile Ser Asn Thr Arg Ala Ala His Ser Gln Phe Glu
            100                 105                 110

Lys Trp Tyr Glu Gly Val Arg Asn Asp Tyr Ala Leu Asn Asp Asn Glu
        115                 120                 125

Met Gln Val Met Leu Asn Gly Leu Met Val Trp Cys Ile Glu Asn Gly
    130                 135                 140

Thr Ser Pro Asp Ile Ser Gly Val Trp Val Met Met Asp Gly Glu Thr
145                 150                 155                 160

Gln Val Asp Tyr Pro Ile Lys Pro Leu Ile Glu His Ala Thr Pro Ser
                165                 170                 175

Phe Arg Gln Ile Met Ala His Phe Ser Asn Ala Ala Glu Ala Tyr Ile
            180                 185                 190

Ala Lys Arg Asn Ala Thr Glu Arg Tyr Met Pro Arg Tyr Gly Ile Lys
        195                 200                 205

Arg Asn Leu Thr Asp Ile Ser Leu Ala Arg Tyr Ala Phe Asp Phe Tyr
    210                 215                 220

Glu Val Asn Ser Lys Thr Pro Asp Arg Ala Arg Glu Ala His Met Gln
225                 230                 235                 240

Met Lys Ala Ala Ala Leu Arg Asn Thr Ser Arg Arg Met Phe Gly Met
                245                 250                 255

Asp Gly Ser Val Ser Asn Lys Glu Glu Asn Thr Glu Arg His Thr Val
            260                 265                 270

Glu Asp Val Asn Arg Asp Met His Ser Leu Leu Gly Met Arg Asn
        275                 280                 285
```

Another nucleic acid suitable in the present invention is the CP gene isolated from the Venezuela ("VE") strain of PRSV, corresponding to SEQ ID NO: 19, as follows:

```
atggctgtgg atgctggttt gaatgggaag ctcaaagaaa aagagaaaaa agaaaaagaa  60
aaagaaaaac agaaagagaa agagaaagat gatgctagtg acggaaatga tgtgtcaact 120
agcacaaaaa ctggagagag agatagagat gtcaatattg ggaccagtgg aactttcact 180
gtccctagga ttaaatcatt tactgataag atgattttac cgagaattaa gggaaagact 240
gtccttaatt taaatcatct tcttcagtat aatccgaaac aaattgacat ttctaatact 300
cgtgccactc agtcgcaatt tgagaaatgg tatgagggag tgagggatga ttatggcctt 360
aatgataatg aaatgcaagt gatgctaaat ggcttgatgg tttggtgcat tgagaatggt 420
acatctccag acatatctgg tgtttgggtt atggtggatg gggaaaccca agttgattat 480
ccaatcaagc ctttaattga gcatgctaca ccgtcattta ggcaaattat ggctcatttt 540
agtaacgcgg cagaagcata cattgcgatg agaaatgcta ctgagaggta catgccgcgg 600
tatggaatca agagaaattt gactgacatc aacctagctc gatacgcttt tgatttctat 660
gaggtgaatt cgaaaacmcc tgatagggct cgtgaagctc acatgcagat gaaggctgca 720
gctttgcgaa acactaatcg cagaatgttt ggtatcgacg gcagtgttag caacaaggaa 780
gaaaacacgg agagacacac agtggatgat gtcaatagag acatgcactc tctcctgggt 840
atgcgcaact aaatactcgc acttgtgtgt ttgtcgagcc tgact                 885
```

SEQ ID NO: 19 encodes the CP of the VE strain of PRSV which has an amino acid sequence corresponding to SEQ ID NO: 20, as follows:

```
Met Ala Val Asp Ala Gly Leu Asn Gly Lys Leu Lys Glu Lys Glu Lys
  1               5                  10                  15

Lys Glu Lys Glu Lys Glu Lys Gln Lys Glu Lys Glu Lys Asp Asp Ala
             20                  25                  30

Ser Asp Gly Asn Asp Val Ser Thr Ser Thr Lys Thr Gly Glu Arg Asp
         35                  40                  45

Arg Asp Val Asn Ile Thr Ser Gly Thr Phe Thr Val Pro Arg Ile Lys
     50                  55                  60

Ser Phe Thr Asp Lys Met Ile Leu Pro Arg Ile Lys Gly Lys Thr Val
 65                  70                  75                  80

Leu Asn Leu Asn His Leu Leu Gln Tyr Asn Pro Lys Gln Ile Asp Ile
                 85                  90                  95

Ser Asn Thr Arg Ala Thr Gln Ser Gln Phe Glu Lys Trp Tyr Glu Gly
            100                 105                 110

Val Arg Asp Asp Tyr Gly Leu Asn Asp Asn Glu Met Gln Val Met Leu
        115                 120                 125

Asn Gly Leu Met Val Trp Cys Ile Glu Asn Gly Thr Ser Pro Asp Ile
    130                 135                 140

Ser Gly Val Trp Val Met Val Asp Gly Glu Thr Gln Val Asp Tyr Pro
145                 150                 155                 160

Ile Lys Pro Leu Ile Glu His Ala Thr Pro Ser Phe Arg Gln Ile Met
                165                 170                 175

Ala His Phe Ser Asn Ala Ala Glu Ala Tyr Ile Ala Met Arg Asn Ala
            180                 185                 190

Thr Glu Arg Tyr Met Pro Arg Tyr Gly Ile Lys Arg Asn Leu Thr Asp
```

-continued

```
        195                 200                 205

Ile Asn Leu Ala Arg Tyr Ala Phe Asp Phe Tyr Glu Val Asn Ser Lys
    210                 215                 220

Xaa Pro Asp Arg Ala Arg Glu Ala His Met Gln Met Lys Ala Ala Ala
225                 230                 235                 240

Leu Arg Asn Thr Asn Arg Arg Met Phe Gly Ile Asp Gly Ser Val Ser
                245                 250                 255

Asn Lys Glu Glu Asn Thr Glu Arg His Thr Val Asp Asp Val Asn Arg
            260                 265                 270

Asp Met His Ser Leu Leu Gly Met Arg Asn
        275                 280
```

Also suitable for use in the present invention are variants of the nucleic acid molecules shown above. An example of a suitable nucleic acid is a nucleic acid molecule which has a nucleotide sequence that is at least 85% similar to the nucleotide sequence of the SEQ ID NOS: 1, 3, 5, 6, 9, 11, 13, 15, 17, and 19 by basic BLAST using default parameters analysis, or which hybridizes to the nucleotide sequence of SEQ ID NOS: 1, 3, 5, 6, 9, 11, 13, 15, 17, and 19 under stringent conditions characterized by a hybridization buffer comprising 5×SSC buffer at a temperature of about 42°-65° C., preferably 56° C.

Fragments of genes encoding PRSV-CP are particularly useful in the present invention. Fragments capable of use in the present invention can be produced by several means. In one method, subclones of the gene encoding the CP of choice are produced by conventional molecular genetic manipulation by subcloning gene fragments. In another approach, based on knowledge of the primary structure of the protein, fragments of a PRSV-CP encoding gene may be synthesized by using the PCR technique together with specific sets of primers chosen to represent particular portions of the protein. These, then, would be cloned into an appropriate vector in either the sense or antisense orientation.

Another example of suitable fragments of the nucleic acids of the present invention are fragments of the genes which have been identified as conserved ("con") regions of the CP proteins, or alternatively, those portions of PRSV-CP nucleotide sequences that have been identified as variable ("var") regions. Sequences identified using DNAStar Mega alignment program as either variable or conserved in a PRSV-CP gene can be amplified using standard PCR methods using forward and reverse primers designed to amplify the region of choice and which include a restriction enzyme sequence to allow ligation of the PCR product into a vector of choice. Combinations of amplified conserved and variable region sequences can be ligated into a single vector to create a "cassette" which contains a plurality of DNA molecules in one vector. The use of conserved and variable regions of PRSV-CP DNA is further detailed below in the Examples.

The present invention also relates to a DNA construct that contains a DNA molecule encoding for a PRSV-CP isolated from any of a variety of PRSV strains, most preferably the TH, KA, KE, YK, ME, BR, JA, OA, and VE strains. This involves incorporating one or more of the nucleic acid molecules of the present invention, or a suitable portion thereof, of the nucleic acid corresponding to SEQ ID NOS: 1, 3, 5, 6, 9, 11, 13, 15, 17, and 19 into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences.

The nucleic acid molecules of the present invention may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA ("T-DNA") is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley, et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, M., "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch, et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use in the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase ("NOS") gene promoter, from *Agrobacterium tumefaciens*, (U.S. Pat. No. 5,034,322 to Rogers et al., which is hereby incorporated by reference in its entirety), the cauliflower mosaic virus ("CaMV") 35S and 19S promoters (U.S. Pat. No. 5,352,605 to Fraley et al., which is hereby incorporated by reference in its entirety), the enhanced CaMV35S promoter ("enh CaMV35S"), the figwort mosaic virus full-length transcript promoter ("FMV35S"), those derived from any of the several actin genes, which are known to be expressed in most cells types (U.S. Pat. No. 6,002,068 to Privalle et al., which is hereby incorporated by reference in its entirety), and the ubiquitin promoter ("ubi"), which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter ("GIP") (Schena et al., "A Steroid-Inducible Gene Expression System for Plant Cells," *Proc. Natl. Acad. Sci.* 88:10421-5 (1991), which is hereby incorporated by reference in its entirety). Other useful promoters include promoters capable of expressing potyvirus proteins in an inducible manner or in a tissue-specific manner in certain cell types where infection is known to occur. These include, for example, the inducible promoters from phenylalanine ammonia lyase, chalcone synthase, extensin, pathogenesis-related protein, and wound-inducible protease inhibitor from potato. Other examples of such tissue specific promoters include seed, flower, or root specific promoters as are well known in the field (U.S. Pat. No. 5,750,385 to Shewmaker et al., which is hereby incorporated by reference in its entirety). For a review on maximizing gene expression, see Roberts and Lauer, *Methods in Enzymology* 68:473 (1979), which is hereby incorporated by reference in its entirety.

The particular promoter selected is preferably capable of causing sufficient expression of the DNA coding sequences to which it is operably linked, to result in the production of amounts of the proteins effective to provide viral resistance, but not so much as to be detrimental to the cell in which they are expressed. The actual choice of the promoter is not critical, as long as it has sufficient transcriptional activity to accomplish the expression of the preselected proteins, where expression is desired, and subsequent conferral of viral resistance to the plants. The promoters selected should be capable of functioning in tissues including, but not limited to, epidermal, vascular, and mesophyll tissues.

The nucleic acid construct of the present invention also includes an operable 3' regulatory region, which provides a functional poly(A) addition signal (AATAAA) 3' of its translation termination codon. This is selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA* 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would suffice for proper expression of the coding sequence of the nucleic acid construct of the present invention.

A vector of choice, suitable promoter, and an appropriate 3' regulatory region can be ligated together to produce the expression systems which contain the nucleic acids of the present invention, or suitable fragments thereof, using well known molecular cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology*, John Wiley & Sons, New York, N.Y., which are hereby incorporated by reference in their entirety.

Once the isolated nucleic acid molecules encoding the various papaya ringspot virus coat proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

Accordingly, another aspect of the present invention relates to a recombinant plant cell containing one or more of the PRSV-CP nucleic acids of the present invention. Basically, this method is carried out by transforming a plant cell with a nucleic acid construct of the present invention under conditions effective to yield transcription of the DNA molecule in response to the promoter. Methods of transformation may result in transient or stable expression of the DNA under control of the promoter. Preferably, the nucleic acid construct of the present invention is stably inserted into the genome of the recombinant plant cell as a result of the transformation, although transient expression can serve an important purpose, particularly when the plant under investigation is slow-growing.

Plant tissue suitable for transformation include without limitation, leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue is often achieved by particle bombardment (Klein et al., "High-Velocity Microprojectiles for Delivering Nucleic Acids Into Living Cells," *Nature* 327:70-73 (1987), which is hereby incorporated by reference in its entirety). In this method, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells (U.S. Pat. Nos. 4,945,050, 5,036,006, and 5,100,792, all to Sanford et al., which are hereby incorporated by reference in their entirety). For papaya, particle gun bombardment has been a particularly successful method (Fitch, M. M., "Stable Transformation of Papaya Via Micro-Projectile Bombardment," *Plant Cell Rep.* 9:189 (1990), and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference). Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign DNA into plant cells. Yet another method of introduction is fusion of protoplasts with other entities, either minicells, cells, lysosomes or other fusible lipid-surfaced bodies (Fraley, et al., *Proc. Natl. Acad. Sci. USA* 79:1859-63 (1982), which is hereby incorporated by reference in its entirety). The DNA molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures, Vol.* 1: (MacMillan Publishing Co., New York, 1983); Vasil I. R. (ed.), *Cell Culture and Somatic Cell Genetics of Plants*, Acad. Press, Orlando, Vol. I, 1984, and Vol. III (1986), and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference it their entirety.

It is known that practically all plants can be regenerated from cultured cells or tissues, including but not limited to, all major species of sugarcane, sugar beets, cotton, fruit trees, and legumes.

Means for regeneration vary from species to species of plants, but generally, a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptll gene which confers kanamycin resistance (Fraley, et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the viral gene by Southern blot hybridization analysis, using a probe specific to the viral genes contained in the given cassette used for transformation (Sambrook et al., “Molecular Cloning: A Laboratory Manual,” Cold Spring Harbor, N.Y.: Cold Spring Harbor Press (1989), which is hereby incorporated by reference in its entirety).

The presence of a viral coat protein gene can also be detected by immunological assays, such as the double-antibody sandwich assays described by Namba et al., “Expression of the Gene Encoding the Coat Protein of Cucumber Mosaic Virus (CMV) Strain WL appears to Provide Protection to Tobacco Plants Against Infection by Several Different CMV Strains,” *Gene* 107:181-188 (1991), which is hereby incorporated by reference in its entirety, as modified by Clark et al., “Characteristics Of the Microplate Method for Enzyme-Linked Immunosorbent Assay For the Detection of plant Viruses,” *J. Gen. Virol.* 34, 475-83 (1977), which is hereby incorporated by reference in its entirety. Potyvirus resistance can also be assayed via infectivity studies as generally described by Namba et al., “Protection of Transgenic Plants Expressing the Coat Protein Gene of Watermelon Virus ii or Zucchini Yellow Mosaic Virus Against Potyviruses,” *Phytopath.* 82:940946 (1992), which is hereby incorporated by reference in its entirety, wherein plants are scored as symptomatic when any inoculated leaf shows veinclearing, mosaic, or necrotic symptoms.

After the expression cassette is stably incorporated in transgenic plants, it can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds or propagules (e.g., cuttings) are recovered from the transgenic plants. These seeds can then be planted in the soil and cultivated using conventional procedures to produce transgenic plants.

The present invention also relates to DNA constructs which contain a plurality of DNA molecules which are derived from one or more genes which encode a papaya ringspot viral coat protein. The PRSV-CP DNA molecules may be derived from one or more strains, including, but not limited to, TH, KE, KA, ME, YK, BR, JA, OA, and VE. Some of the PRSV-CP DNA molecules may be a fragment of the nucleic acid sequence of the CP(s) of choice which by itself is too short, i.e., does not contain sufficient nucleotide sequence, to impart its respective trait when placed in an vector and used to transform plant cells as described above. Collectively, however, this plurality of DNA molecules impart their trait to the transformed plant. The trait which is imparted is resistance to the PRSV strain from which any given DNA molecule in the construct is derived. Suitable nucleic acids for this construct include fragments of a PRSV CP-encoding DNA molecule, of any strain, including but not limited to, TH, KE, KA, ME, YK, BR, JA, OA, and VE. The DNA molecules are inserted in the construct as less than full-length DNA, preferably in the range of about 200 bp of the full-length PRSV-CP DNA molecule. The 200 bp fragments are preferably chosen from the conserved and variable regions of CP-encoding DNA. There is no need to include separate promoters for each of the fragments; only a single promoter is required. Moreover, such viral gene fragments can preferably be incorporated in a single expression system to produce transgenic plants with a single transformation event.

The present invention also relates to a DNA construct containing a fusion gene which includes a trait DNA molecule which has a length insufficient to independently impart a desired trait to plants transformed with the trait molecule, operatively coupled to a silencer molecule effective to achieve post-transcriptional gene silencing. The trait DNA molecule and the silencer molecule collectively impart the trait to plants transformed with the construct. The trait DNA molecules of this DNA construct are derived from a gene encoding a papaya ringspot viral coat protein from a papaya ringspot virus strains which include, but are not limited to TH, KE, KA, ME, YK, BR, JA, OA, and VE. The fragments of trait DNA molecules are subcloned into the fusion gene cassette. Suitable DNA fragments are those of about 200 bp which derive from the variable and conserved regions of the CP-encoding molecules of choice. The silencer molecule of the construct of the present invention can be selected from virtually any nucleic acid which effects gene silencing. This involves the cellular mechanism to degrade mRNA homologous to the transgene mRNA. The silencer DNA molecule can be heterologous to the plant, need not interact with the trait DNA molecule in the plant, and can be positioned 3' to the trait DNA molecule. For example, the silencer DNA molecule can be a viral cDNA molecule, including, without limitation, a gene encoding a replicase, a movement protein, or a nucleocapsid protein; a green fluorescence protein encoding DNA molecule, a plant DNA molecule, or combinations thereof.

In any of the constructs of the present invention, the DNA molecule conferring disease resistance can be positioned within the DNA construct in the sense (5'→3') orientation. Alternatively, it can have an antisense (3'→5') orientation. Antisense RNA technology involves the production of an RNA molecule that is complementary to the messenger RNA molecule of a target gene. The antisense RNA can potentially block all expression of the targeted gene. In the anti-virus context, plants are made to express an antisense RNA molecule corresponding to a viral RNA (that is, the antisense RNA is an RNA molecule which is complementary to a “plus” (+) sense RNA species encoded by an infecting virus). Such plants may show a slightly decreased susceptibility to infection by that virus. Such a complementary RNA molecule is termed antisense RNA.

It is possible for the DNA construct of the present invention to be configured so that the trait and silencer DNA molecules encode RNA molecules which are translatable. As a result, that RNA molecule will be translated at the ribosomes to produce the protein encoded by the DNA construct. Production of proteins in this manner can be increased by joining the cloned gene encoding the DNA construct of interest with synthetic double-stranded oligonucleotides which represent a viral regulatory sequence (i.e., a 5' untranslated sequence) (U.S. Pat. No. 4,820,639 to Gehrke, and U.S. Pat. No. 5,849,527 to Wilson, which are hereby incorporated by reference in their entirety).

Alternatively, the DNA construct of the present invention can be configured so that the trait and silencer DNA molecules encode mRNA which is not translatable. This is achieved by introducing into the DNA molecule one or more premature stop codons, adding one or more bases (except multiples of 3 bases) to displace the reading frame, removing the translation initiation codon, etc. See U.S. Pat. No. 5,583,021 to Dougherty et al., which is hereby incorporated by reference in its entirety. The subject DNA construct can be incorporated in cells using conventional recombinant DNA technology, such as described in detail above.

Another aspect of the present invention is a method to confer resistance to PRSV to plants. This involves transforming susceptible plants with one or more of the nucleic acid constructs of the present invention, testing for transformation using a marker inherent in the vector, selecting transgenics, and regenerating and reproducing the transgenic plants as described above. The expression system of the present invention can be used to transform virtually any plant tissue under suitable conditions. Transformed cells can be regenerated into whole plants such that the PRSV-transgene imparts resistance to PRSV in the intact transgenic plants. In either case, the plant cells transformed with the recombinant DNA expression system of the present invention are grown and caused to express the DNA molecule or molecules in the constructs of the present invention, and, thus, to impart papaya ringspot resistance.

While not wishing to be bound by theory, by use of the constructs of the present invention, it is believed that post-transcriptional gene silencing is achieved. More particularly, the silencer DNA molecule is believed to boost the level of heterologous RNA within the cell above a threshold level. This activates the degradation mechanism by which viral resistance is achieved.

Transgenic plants which show post-transcription gene silencing-derived resistance establish the highly resistant state and prevent virus replication. A chimeric transgene consisting of a silencer DNA (e.g., GFP) fused with various small nontranslatable fragment viral genome would be preferred for viral resistance. There are several advantages. First, the silencer DNA can increase the induced gene silencing. Second, the chimeric nature of the gene would provide multiple virus resistance. Third, nontranslatable construction produces no protein, thus reducing the possible complementation of naturally occurring mutants and transencapsidation of other viruses. Fourth, the small fragment also reduces the possibility of recombination with other viral genomes.

Absent a complete understanding of the mechanism(s) of viral resistance conferred through this type of genetic manipulation, optimization of the production of viral resistant transgenics is still under study. Thus, the degree of resistance imparted to a given transgenic plant (high, medium, or low efficacy) is unpredictable. However, it has been noted that when combinations of viral gene expression cassettes are placed in the same binary plasmid, and that multigene cassette containing plasmid is transformed into a plant, the viral genes all exhibit substantially the same degrees of efficacy when present in transgenic plants. For example, if one examines numerous transgenic lines containing two different intact viral gene cassettes, the transgenic line will be immune to infection by both viruses. Likewise if a transgenic line exhibits a delay in symptom development to one virus, it will also exhibit a delay in symptom development to the second virus. Finally, if a transgenic line is susceptible to one of the viruses it will be susceptible to the other. This phenomenon is unexpected. If there were not a correlation between the efficacy of each gene in these multiple gene constructs, this approach as a tool in plant breeding would probably be prohibitively difficult to use. The probability of finding a line with useful levels of expression can range from 10-50%, depending on the species involved (U.S. Pat. No. 6,002,072 to McMaster et al., which is hereby incorporated by reference in its entirety).

The present invention will be further described by reference to the following detailed examples.

EXAMPLES

Example 1

Amplification and Cloning of CP Variable Region DNAs

Total RNA was extracted from PRSV-infected papaya plants. Different PRSV-CP gene fragments, each about 200 bp, from Taiwan (YK), Keaau (KE), and Thailand (TH) strains were amplified by reverse-transcription and polymerase-chain-reaction (RT-PCR) and extracted from agarose gels. The primers used to amplify the variable region of the PRSV-CP gene of strains YK, KE, and TH are shown in Table 1.

TABLE 1

| PRSV Strain | Product (bp) | Primer position | Primer Sequence (SEQ ID NO) |
|---|---|---|---|
| YKvar | 209 | | |
| 5'YKvarXba | | 21-39 | 5' GAGAtctaga TAATGA*TACCGGTCTGAATGAGAAG* 3' (SEQ ID NO: 21) |
| 3'YkvarXho | | 212-229 | 5' GGATctcgag *AGATCATCTTATCAGTAA* 3' (SEQ ID NO: 22) |
| KEvar | 209 | | |
| 5'KEvarXho | | 21-39 | 5' TAGActcgag *TGCTGGTTTGAATGAAAAA* 3 (SEQ ID NO: 23) |
| 3'KEvarSma | | 211-229 | 5' CGATcccggg *GAATCAACTTATCAGTAA* 3' (SEQ ID NO: 24) |
| THvar | 206 | | |
| 5'THvarSma | | 21-39 | 5' TATAcccggg *TGCTGGTCTTAATGAGAAG* 3' (SEQ ID NO: 25) |
| 3'THvarBam | | 209-226 | 5' CTACggatcc *AAATCATCTTGTCGGTAA* 3' (SEQ ID NO: 26) |

Restriction enzyme sequence is shown in small letters;
the stop codon is shown in caps, without italics;
viral sequences are italicized.

Following amplification using conventional PCR techniques, the amplified fragments were digested with the appropriate restriction enzymes. A restriction enzyme XbaI-XhoI digested YK fragment (209 bp) was first ligated into the pEPJ vector. A XhoI-SmaI digested KE fragment (209 bp) was ligated behind (i.e., at the 3' end of) the YK fragment and then a SmaI-BamHI digested TH fragment (206 bp) was ligated behind the KE. The resultant clone, pEPJ-YKT, shown in FIG. 1A, contains the variable region of CP from YK-KE-TH in the 5'→3' direction. Following a HindIII-KpnI restriction digest, the pEPJ-YKT expression cassette was ligated into the HindIII-KpnI cloning site of transformation vector pGA482G, shown in FIG. 1B, resulting in clone pTi-EPJ-YKT. Cesium chloride purified pTi-EPJ-YKT was then used for host cell transformation by particle gun bombardment.

Example 2

Cloning of CP Variable Regions into Silencer Construct

Figure 2:
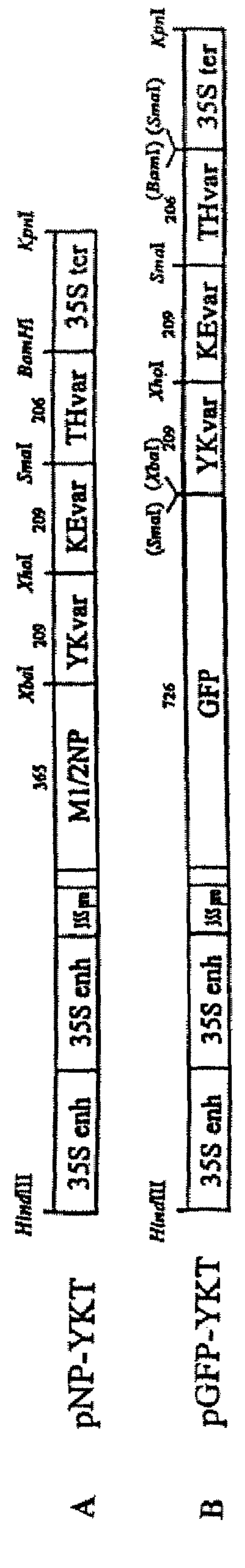
FIGS. 2A-B show the expression vectors used for cloning and subcloning the silencer-PRSV-CP construct.
Figure 3:
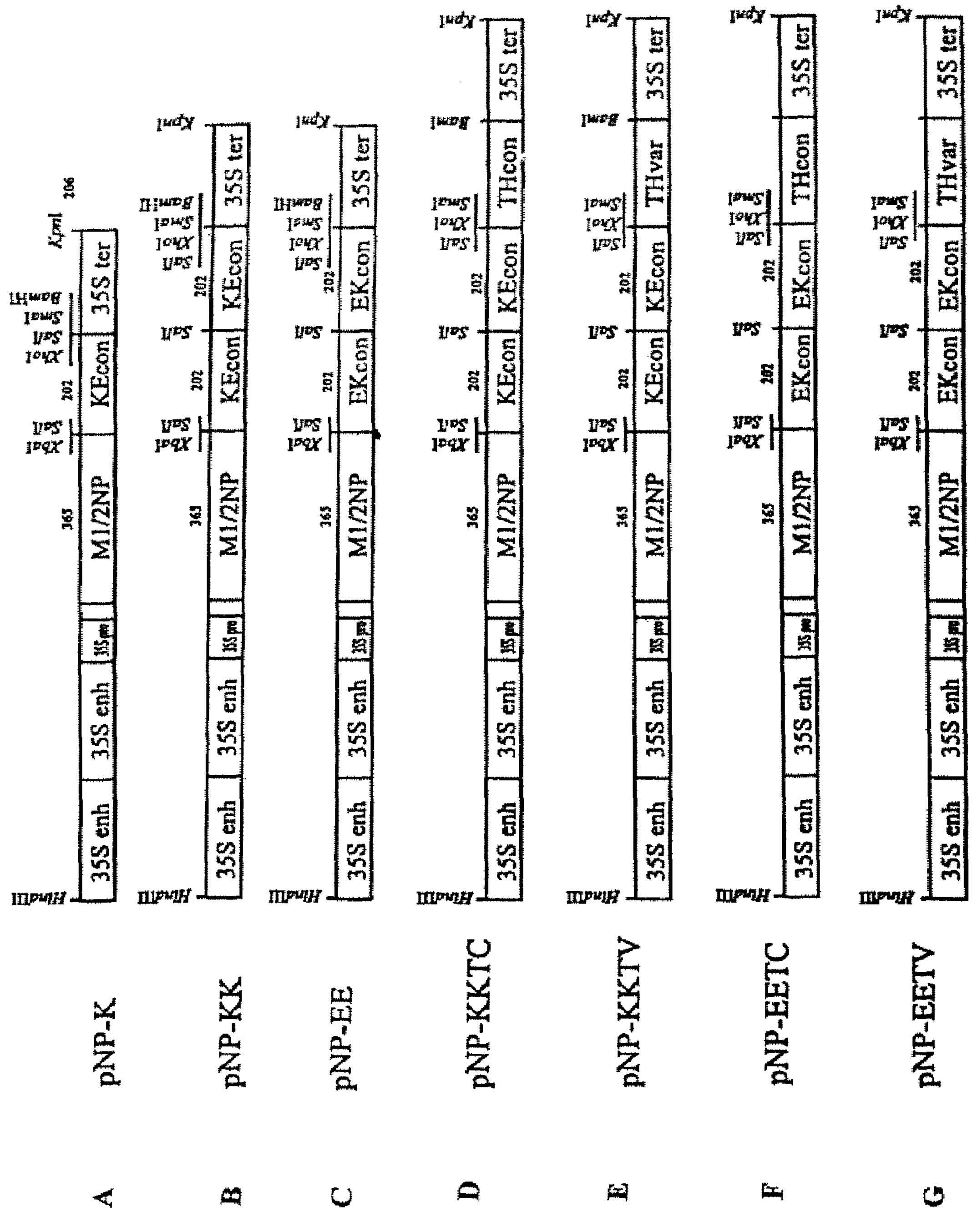
FIGS. 3A-G show various PRSV-CP DNA molecules ligated to the silencer molecule (M 1/2 NP) in an expression vector.

Fragments XbaI/BamHI from pEPJ-YKT were ligated into other expression vectors pNP, shown in FIG. 2A, and pGFP, shown in FIG. 2B, creating pNP-YKT and pGFP-YKT, respectively. "M1/2 NP" shown in FIG. 2A refers to a fragment consisting of approximately one half (387-453 bp) of the gene encoding the nucleocapsid protein ("N" or "NP" gene) of the viral genome of the tomato spotted wilt virus ("TSWV"), a tospovirus that causes crop damage worldwide. Expression of large fragments (approximately ½ or greater) of the N gene of TSWV have been shown to confer high levels of resistance to TSWV-BL in 20-51% of R1 plants transformed with the fragment, and tolerance to tospovirus infection in 4-22% of R1 plants isolate but not to the distantly related Impatiens necrotic spot virus ("INSV") (Law et al., "The M RNA of Impatiens Necrotic Spot Tospovirus (Bunyaviridae) Has an Ambisense Genomic Organization," *Virology,* 188:732-41 (1992), which is hereby incorporated by reference in its entirety) or groundnut ringspot virus ("GRSV") (Pang et al., "The Biological Properties of a Distinct Tospovirus and Sequence Analysis of Its mRNA," *Phytopathology,* 83:728-33 (1993), which is hereby incorporated by reference in its entirety). The N gene of TSWV is an example of a gene derived from the viral genome that is useful as a silencer molecule in the nucleic acid constructs of the present invention. Restriction enzyme HindIII/KpnI digested fragments from these two expression vectors were then ligated into the HindIII/KpnI cloning site of the transformation vector pGA482G, resulting in clones pTi-NP-YKT and pTi-GFP-YKT. Cesium chloride purified pTi-NP-YKT and pTi-GFP-YKT were then used for host cell transformation by particle gun bombardment.

Example 3

Amplification and Cloning of CP Conserved Region DNAs

Total RNA was extracted from PRSV-infected papaya plants. Different PRSV-CP gene fragments, each about 200 bp, from Keaau (KE) and Thailand (TH) were amplified by RT-PCR. The primers used to amplify the conserved region of the PRSV-CP gene of strains KE and TH are shown in Table 2.

TABLE 2

| PRSV Strain | Product (bp) | Primer position | Primer Sequence (SEQ ID NO) |
|---|---|---|---|
| KEcon | 203 | | |
| 5'KEconXbaSal | | 649-686 | 5'TCAAtctagagtcgac*GCTAGATATGCTTTCGAC* 3' (SEQ ID NO: 27) |
| 3'KEconXhoSal | | 834-851 | 5'AAGTctcgaggtcgac*CCCAGGAGAGAGTGCATG* 3' (SEQ ID NO: 28) |
| THcon | 203 | | |
| 5'THconSma | | 646-683 | 5'AATAcccggg*GCTAGATATGCTTTCGAC*_3' (SEQ ID NO: 29) |
| 3'THconBam | | 831-848 | 5'TTATggatcc*CCTAGGAGAGAGTGCATG* 3 (SEQ ID NO: 30) |

Restriction enzyme sequence is shown in small letters;
the stop codon is shown in caps, without italics;
viral sequences are italicized.

Constructs containing the silencer molecule 1/2 NP are shown in FIGS. 3A-G. These constructs are designated herein as clone pNP-$X_n$, where "X" denominates of PRSV strain from which the CP DNA is derived, and "n" represents the number fragments of "X" in the cassette. When the DNA is inserted in the sense orientation, "X" is the first initial of the strain, for example, "K" for KE, "T" for TH. When a fragment is inserted in the antisense orientation, the strain acronym is flipped, for example, KE becomes EK, and "X" becomes the first initial of the antisense designation. For example, for an antisense fragment of KE, "X" becomes "E." Translatable and nontranslatable forms of the DNA molecule are further designated with the prefix "TL" and "NTL", respectively.

Clone pNP-K, shown in FIG. 3A, was obtained by ligating a single 203 bp XbaI/XhoI digested KE DNA fragment in a sense orientation into the expression vector pNP containing the 365 bp M1/2NP DNA molecule. Clone pNP-KK, shown in FIG. 3B, and pNP-EE, shown FIG. 3C, containing sense and antisense KE fragments, respectively, were obtained by ligating a SalI digested KE DNA fragment into pNP-K. Clone pNP-KKTC, shown in FIG. 3D, pNP-KKTV, shown in FIG. 3E, pNP-EETC, shown in FIG. 3F; and pNP-EETV, shown in FIG. 3G, were obtained by ligating a SmaI/BamHI digested KE fragment from the conserved region (KEcon) or from the variable region (KEvar) into pNP-KK or pNP-EE.

The pNP clones were HindIII/KpnI digested from the expression vectors, and ligated into the HindIII/KpnI cloning site of the transformation vector pGA482G, resulting in clones pTi-NP-K, pTi-NP-KK, pTi-NP-EE, pTi-NP-KKTC, pTi-NP-KKTV, pTi-NP-EETC and pTi-NP-EETV. Cesium chloride purified pTi-NP-clones were then used for host cell transformation by particle gun bombardment.

Example 4

Amplification and Cloning of Full Length Translatable and Nontranslatable KE

Figure 4:
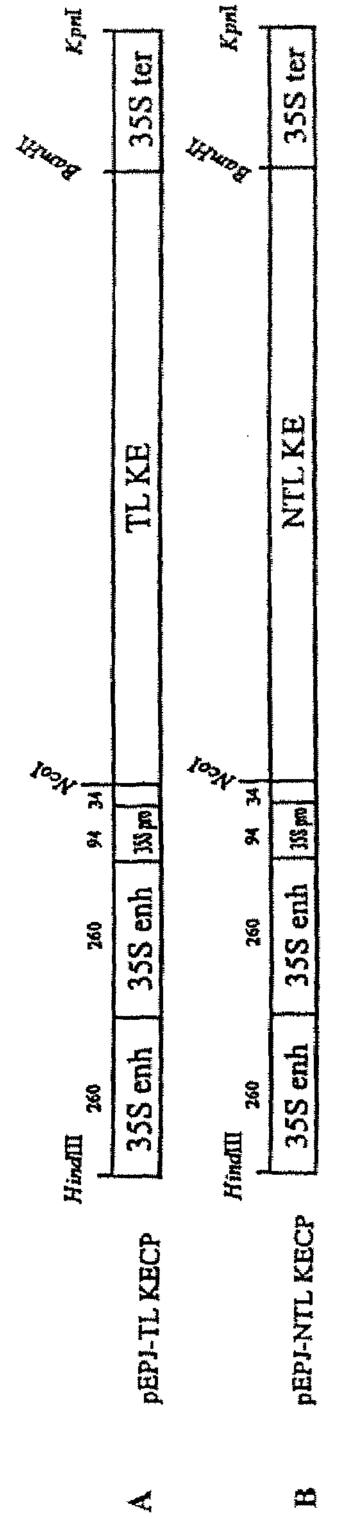
FIG. 4A shows the a full-length (1 Kb) KE-CP DNA molecule encoding a translatable RNA for PRSV-CP ligated into the expression vector pEPJ.
FIG. 4B shows a full-length (1 Kb) KE-CP DNA molecule encoding a non-translatable RNA for PRSV-CP ligated into the expression vector pEPJ.
Figure 5:
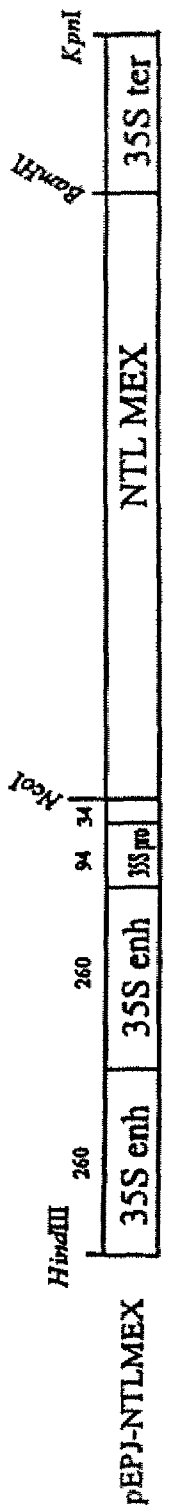
FIG. 5 shows a 855 bp NcoI/BamHI Mexico PRSV-CP DNA molecule ligated into the expression vector pEPJ.

Two full-length KE-CP constructs, shown in FIG. 4, start from the first CP cut site which is 60 nt upstream from the second CP cut site. The primers used for amplification and construction of pEPJ-TL KE and pEPJ-NTL KE are shown in Table 3.

TABLE 3

| PRSV Strain | Product (bp) | Primer Sequence (SEQ ID NO) |
|---|---|---|
| TL KE | 921 | |
| 55'KETL | | 5'AGCTAAccatggAA*TCAAGGAGCACTGATGATTATC* 3'_(SEQ ID NO: 31) |
| 3'KE10117 | | 5'ATTTggatcccggg*GTTGCGCATGCCCAGGAGAGAG* 3' (SEQ ID NO: 32) |
| NTL KE | 921 | |
| 5'KENTL | | 5' AGCTAAccatggAATAATGG*AGCACTGATGATTATC* 3'_(SEQ ID NO: 33) |
| 3'KE10117 | | 5'ATTTggatcccggg*GTTGCGCATGCCCAGGAGAGAG* 3' (SEQ ID NO: 34) |

Restriction enzyme sequence is shown in small letters;
the stop codon is shown in caps, without italics;
viral sequences are italicized.

Following amplification, the NcoI/BamHI digested PCR KECP fragments were ligated into pEPJ vector, as shown in FIG. 4. Using HindII/KpnI, the expression cassette was then subcloned into the transformation vector pGA482G.

Example 5

Amplification and Cloning of MEX CP

The primers used for amplification and preparation of construct pEPJ-MEX CP are shown in Table 4.

TABLE 4

| PRSV Strain | Product (bp) | Primer Sequence (SEQ ID NO) |
|---|---|---|
| NTL Mex | | |
| 5'MEXXbaNco | 855 | 5'CGAtctagaccattggAATAATGA*TCCAAGAATGAAGC* 3' (SEQ ID NO: 35) |
| 3'MEXBAM | | 5'CTTAggatcc*GTTGCGCATACCCAGGAGAGA* 3' 3' (SEQ ID NO: 36) |

Restriction enzyme sequence is shown in small letters;
the stop codon is shown in caps, without italics;
viral sequences are italicized.

Example 6

Transformation of Papaya with PRSV-CP DNA Constructs

Papaya embryos were bombarded with DNA constructs prepared as described above and shown in FIGS. 2-5. The transformation procedure was followed as described in Cai et al., "A Protocol for Efficient Transformation and Regeneration of *Carica papaya* L. In Vitro," *Cell Devel. Biol-Plant* 35: 61-69 (1999), which is hereby incorporated by reference in its entirety. Plasmid DNA was purified by ethidium bromide CsCl gradient (Ausubel et al., "CsCl/Ethidium Bromide Preparations of Plasmid DNA," *Current Protocols in Molec Biol.* unit 2.9.1-2.9.20 (1995), which is hereby incorporated by reference in its entirety), ethanol precipitated and suspended in water. Immature zygotic embryos were extracted from seeds of immature green 'Sunrise' or 'Kapoho' papaya and placed on induction medium and kept in the dark. Zygotic embryos with their somatic embryo clusters were placed on Whatman #2 filter paper and spread. The somatic embryos were allowed to proliferate, and following this, the embryos were spread firmly onto fresh filter paper and bombarded with tungsten-coated plasmid DNA. Seven days after bombardment, materials were transferred to induction medium containing kanamycin at 75 mg/L. After four weeks, the kanamycin level was raised to 150 mg/L. After a few weeks in kanamycin medium, actively growing embryo clusters were transferred to kanamycin-free medium. When the embryos developed a pale ivory color and appeared as finger-like extensions, they were transferred to maturation medium for two to four weeks. Mature somatic embryos were transferred to germination medium and then developed into plantlets with dark green leaves and root initials. Those plantlets were transferred to baby jars with rooting medium and transferred to the greenhouse.

Transgenic lines from the germination medium were analyzed by PCR to confirm that the virus gene was in the plantlets. Northern blots were carried out to detect the level of RNA expressed in transgenic lines, and the copy number of the transgene in the transgenic plants was determined by Southern blot analysis.

Following transfer to the greenhouse, transgenic plants were challenged with the KE strain of PRSV. Plants were thereafter monitored for viral symptoms. If no disease symptoms appeared after approximately 4 weeks post-inoculation, those plants were challenged with a different PRSV strain to test for cross-resistance.

Example 7

Resistance Imparted to PRSV by Transgenes 219 transgenic lines containing the various PRSV DNA constructs of the present invention, as described above, were transferred to the greenhouse. Inoculation with KE virus was carried out on 90 plant lines transformed with at least one KE-containing DNA construct. Of those 90 lines challenged with PRSV-KE, 26 lines showed resistance and 64 lines were susceptible.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated nucleic acid molecule encoding a papaya ringspot virus coat protein, wherein the nucleic acid molecule either: 1) has the nucleotide sequence of SEQ ID NOs: 1, 3, 5, 6, 15, 17, or 19 or 2) encodes the amino acid sequence having SEQ ID NOs: 2, 4, 7, 8, 16, 18, or 20.

2. A DNA construct comprising:

the nucleic acid molecule according to claim 1 and an operably linked promoter and 3' regulatory region.

3. A DNA expression vector comprising:

the DNA construct according to claim 2.

4. A host cell transduced with a DNA construct according to claim 2.

5. The host cell according to claim 4, wherein the cell is selected from the group consisting of a bacterial cell, yeast cell, and a plant cell.

6. A transgenic plant transformed with a DNA construct according to claim 2.

7. The transgenic plant according to claim 6, wherein the plant is papaya.

8. A transgenic plant seed transformed with a DNA construct according to claim 2.

9. The transgenic plant seed according to claim 8, wherein the plant is papaya.

10. A method of imparting resistance to papaya plants against papaya ringspot virus comprising:

transforming a papaya plant with a DNA construct according to claim 2.

11. The isolated nucleic acid molecule according to claim 1, wherein the nucleic acid molecule has the nucleotide sequence of SEQ ID NOs: 1, 3, 5, 6, 15, 17, or 19.

12. The isolated nucleic acid molecule according to claim 1, wherein the nucleic acid molecule encodes the amino acid sequence having SEQ ID NOs: 2, 4, 7, 8, 16, 18, or 20.

* * * * *